US010614587B2

(12) United States Patent
Umanskiy et al.

(10) Patent No.: US 10,614,587 B2
(45) Date of Patent: Apr. 7, 2020

(54) MEASUREMENT OF SYRINGE GRADUATION MARKS USING A VISION SYSTEM AND RELATED FUNDAMENTAL FREQUENCY PROCESSING

(71) Applicant: BAXTER CORPORATION ENGLEWOOD, Englewood, CO (US)

(72) Inventors: Yuriy Konstantinovich Umanskiy, Centennial, CO (US); Cari Lyn Heffner, Castle Rock, CO (US); James Robert Hutchison, Denver, CO (US)

(73) Assignee: BAXTER CORPORATION ENGLEWOOD, Englewood, CO (US)

( * ) Notice: Subject to any disclaimer, the term of this patent is extended or adjusted under 35 U.S.C. 154(b) by 0 days.

(21) Appl. No.: 16/066,974

(22) PCT Filed: Dec. 22, 2016

(86) PCT No.: PCT/US2016/068242
§ 371 (c)(1),
(2) Date: Jun. 28, 2018

(87) PCT Pub. No.: WO2017/116961
PCT Pub. Date: Jul. 6, 2017

(65) Prior Publication Data
US 2019/0019306 A1 Jan. 17, 2019

Related U.S. Application Data

(60) Provisional application No. 62/272,789, filed on Dec. 30, 2015.

(51) Int. Cl.
G06T 7/62 (2017.01)
G01F 25/00 (2006.01)
(Continued)

(52) U.S. Cl.
CPC ............ *G06T 7/62* (2017.01); *A61M 5/1782* (2013.01); *A61M 5/31* (2013.01); *G01B 11/00* (2013.01);
(Continued)

(58) Field of Classification Search
CPC .... G06T 7/62; G06T 7/50; G06T 7/80; G06T 2207/20056; A61M 5/31; A61M 5/1782;
(Continued)

(56) References Cited

U.S. PATENT DOCUMENTS 6,628,409 B2   9/2003  Rotsch
9,101,534 B2 * 8/2015  Bochenko ............ A61J 1/2096
(Continued)

FOREIGN PATENT DOCUMENTS

GB    2220743 A  *  1/1990  ............ G01B 11/14
GB    2220743 A     1/1990
(Continued)

OTHER PUBLICATIONS

Mukherjee et al, A syringe injection rate detector employing a dual hall effect sensor configuration (Year: 2013).*
(Continued)

*Primary Examiner* — Shan E Elahi
(74) *Attorney, Agent, or Firm* — K&L Gates LLP

(57) ABSTRACT

Vision system for measurement of a pitch of graduated marks on a syringe. The vision system may utilize a frequency domain representation of image data to measure the pitch. Furthermore, data processing techniques such as interpolation, windowing, and/or calibration may be utilized in connection with the measurement. In turn, the pitch of the graduated marks may be used in connection with automated filing of the syringe such that the syringe is filled based on and according to the graduated marks on the syringe.

20 Claims, 19 Drawing Sheets

(51) Int. Cl.

| | |
|---|---|
| *G01B 11/00* | (2006.01) |
| *G01B 21/04* | (2006.01) |
| *A61M 5/178* | (2006.01) |
| *G01B 11/02* | (2006.01) |
| *G06T 7/80* | (2017.01) |
| *G06T 7/50* | (2017.01) |
| *A61M 5/31* | (2006.01) |
| *H04N 5/225* | (2006.01) |

(52) U.S. Cl.
CPC ............ *G01B 11/02* (2013.01); *G01B 21/042* (2013.01); *G01F 25/0084* (2013.01); *G01F 25/0092* (2013.01); *G06T 7/50* (2017.01); *G06T 7/80* (2017.01); *H04N 5/225* (2013.01); *A61M 2005/3114* (2013.01); *A61M 2005/3126* (2013.01); *A61M 2205/3306* (2013.01); *A61M 2205/3389* (2013.01); *A61M 2205/50* (2013.01); *A61M 2205/702* (2013.01); *G06T 2207/20056* (2013.01)

(58) Field of Classification Search
CPC ...... A61M 2205/50; A61M 2205/3306; A61M 2205/702; A61M 2205/3389; A61M 2005/3126; A61M 2005/3114; H04N 5/225; G01F 25/0084; G01F 25/0092; G01B 11/02; G01B 21/042; G01B 11/00
USPC ......................................................... 348/135
See application file for complete search history.

(56) References Cited

U.S. PATENT DOCUMENTS

| | | | | |
|---|---|---|---|---|
| 9,669,167 | B2 * | 6/2017 | Lockhart | ............... A61B 5/4839 |
| 2006/0178578 | A1 * | 8/2006 | Tribble | ................... B65B 3/003 |
| | | | | 600/432 |
| 2007/0088285 | A1 * | 4/2007 | Sharp | ................ A61M 5/31525 |
| | | | | 604/187 |
| 2012/0320190 | A1 * | 12/2012 | Natroshvili | ............. G06T 5/006 |
| | | | | 348/135 |
| 2013/0177260 | A1 * | 7/2013 | Fujii | .................... H04N 1/4092 |
| | | | | 382/309 |
| 2015/0302845 | A1 * | 10/2015 | Nakano | ................... G10L 13/02 |
| | | | | 704/267 |
| 2015/0305982 | A1 * | 10/2015 | Bochenko | ............. A61J 1/2096 |
| | | | | 604/404 |
| 2015/0347714 | A1 * | 12/2015 | Lockhart | ............... A61B 5/4839 |
| | | | | 435/14 |
| 2019/0019306 | A1 * | 1/2019 | Umanskiy | ................. G06T 7/62 |

FOREIGN PATENT DOCUMENTS

| | | | |
|---|---|---|---|
| WO | 01/86269 A1 | 11/2001 | |
| WO | WO-0186269 A1 * | 11/2001 | ......... G01N 21/8903 |

OTHER PUBLICATIONS

Office Action for related European Application No. 16826570.0; action dated Jun. 12, 2019; (6 pages).
R. Rotinat et al; Three Optical Procedures for Local Large-Strain Measurement; Strain, Blackwell Publishing Ltd., Aug. 1, 2001; vol. 37, No. 3; pp. 89-98.
International Preliminary Report on Patentability for related International Application No. PCT/US2016/068242; reported dated Jul. 3, 2018; (13 pages).
International Search Report for related International Application No. PCT/US2016/068242; report dated Jun. 6, 2017; (6 pages).
Written Opinion for related International Application No. PCT/US2016/068242; report dated Jun. 6, 2017; (12 pages).

* cited by examiner

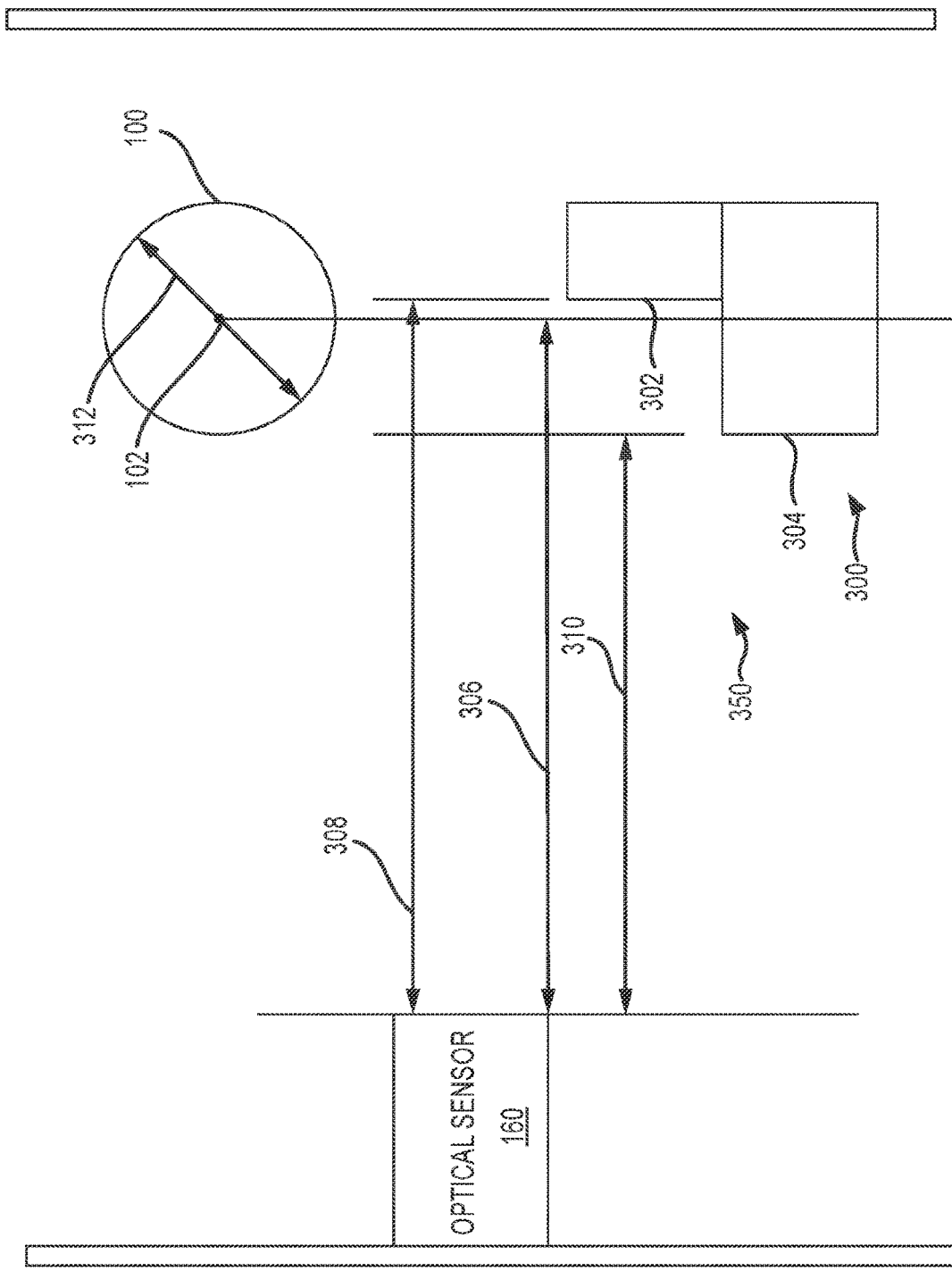

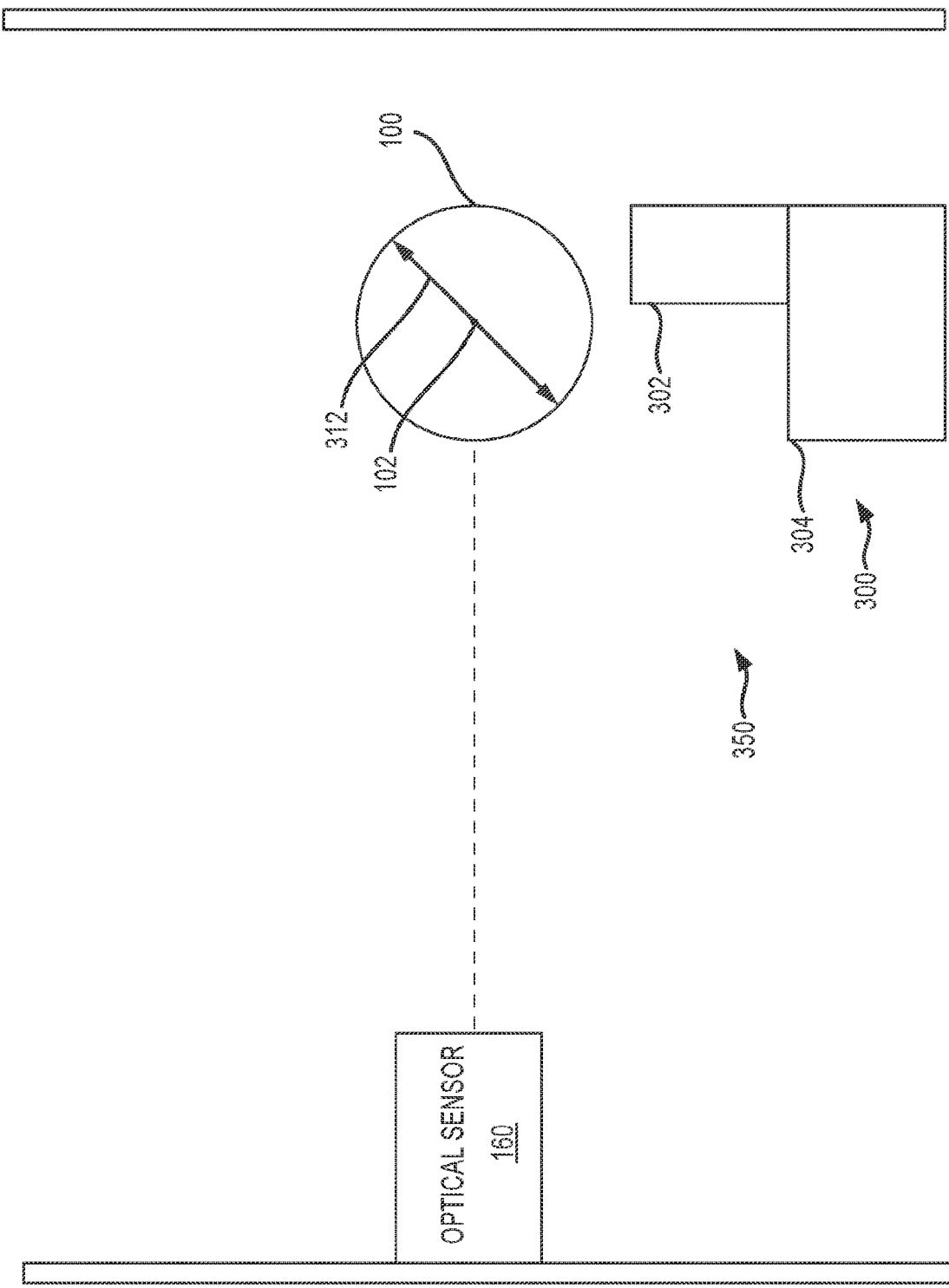

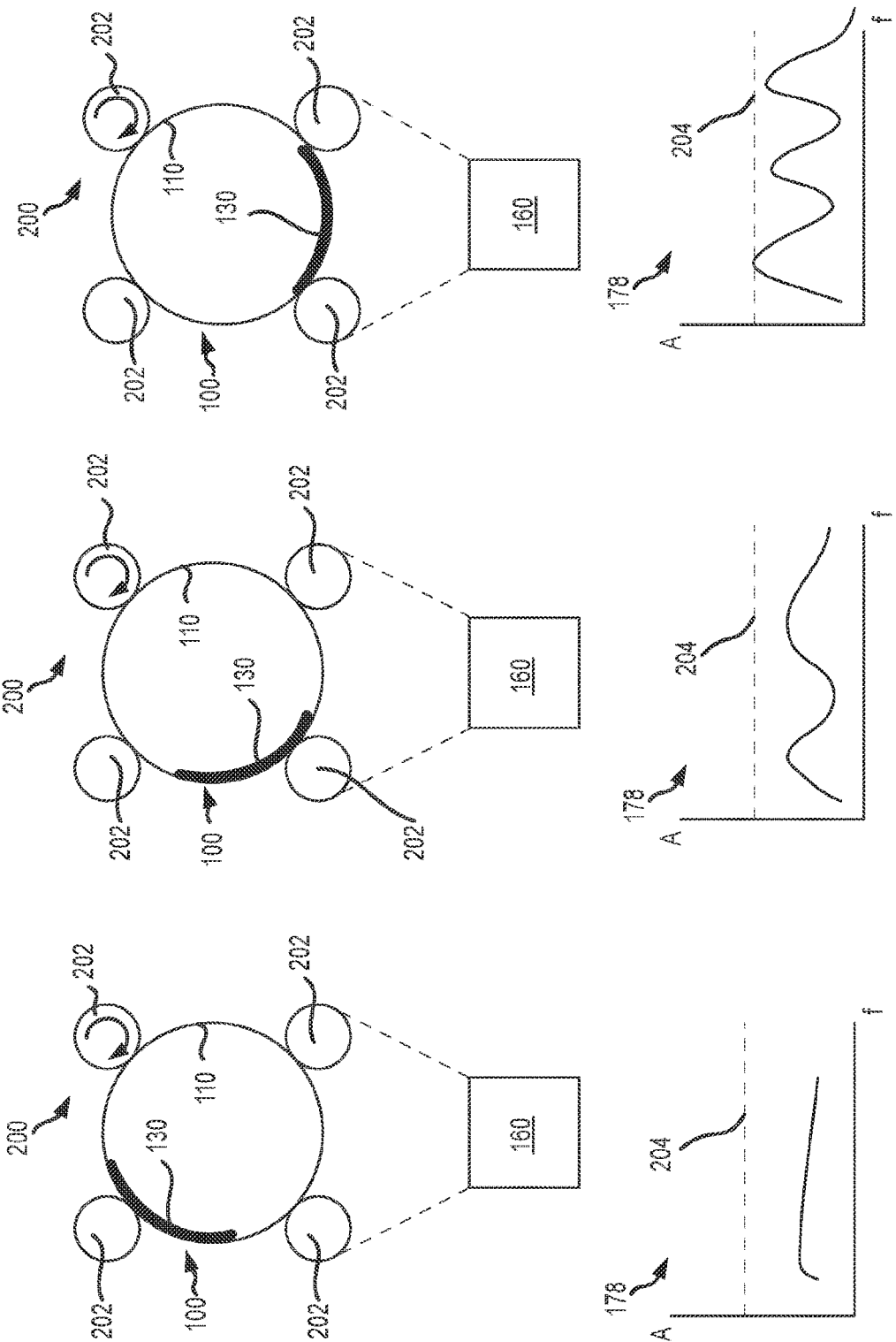

MEASUREMENT OF SYRINGE GRADUATION MARKS USING A VISION SYSTEM AND RELATED FUNDAMENTAL FREQUENCY PROCESSING

CROSS-REFERENCE TO RELATED APPLICATIONS

The present application is a National Stage of International Application No. PCT/US2016/068242, filed on Dec. 22, 2016, which claims priority to U.S. Provisional Patent Application No. 62/272,789 filed on Dec. 30, 2015, entitled "MEASUREMENT OF SYRINGE GRADUATION MARKS USING A VISION SYSTEM", which is incorporated herein by reference in its entirety. This application relates to and incorporates by reference the co-owned U.S. Provisional Patent Application No. 62/272,786 filed on Dec. 30, 2015 entitled "SYRINGE POSITIONING APPARATUS AND METHOD". This application relates to and incorporates by reference the co-owned U.S. Provisional Patent Application No. 62/272,794 filed on Dec. 30, 2015 entitled "CAPACITIVE SINGLE PLATE BUBBLE DETECTOR". This application relates to and incorporates by reference the co-owned U.S. patent application Ser. No. 14/984,022 filed on Dec. 30, 2015 entitled "SOURCE FLUID INLET ASSEMBLY FOR AUTOMATED FILLING DEVICE". This application relates to and incorporates by reference the co-owned U.S. Provisional Patent Application No. 62/272,798 filed on Dec. 30, 2015 entitled "SYRINGE GRIPPING APPARATUS AND METHOD". This application relates to and incorporates by reference the co-owned U.S. patent application Ser. No. 14/984,285 filed on Dec. 30, 2015 entitled "SYRINGE PLUNGER POSITION APPARATUS AND METHOD". This application relates to and incorporates by reference the co-owned U.S. patent application Ser. No. 15/360,365 filed on Nov. 23, 2016 entitled "LABEL APPLICATOR FOR SYRINGE LABELING". This application relates to and incorporates by reference the co-owned U.S. Provisional Patent Application No. 62/272,816 filed on Dec. 30, 2015 entitled "INLET TUBE SET FOR SOURCE INGREDIENT DELIVERY". This application relates to and incorporates by reference the co-owned U.S. patent application Ser. No. 14/984,913 filed on Dec. 30, 2015 entitled "TIP CAP FOR AUTOMATIC SYRINGE FILLING APPARATUS". This application relates to and incorporates by reference the co-owned U.S. patent application Ser. No. 15/179,643 filed on Jun. 10, 2016 entitled "TAMPER EVIDENT SYRINGE TIP CAP".

BACKGROUND

The use of syringes is pervasive in medical care. Drugs, therapies, medicaments, or other substances may be administered to, and/or prepared for, patients using syringes. In this regard, most syringes include graduation marks that assist in measurement of the volume of fluid drawn into a syringe.

Given the pervasiveness of syringes, pharmacies often prepare a large number of syringes for use in the provision of medical care. Pharmacy technicians or other individuals tasked with preparation of medical treatments often use syringes. The syringes may be used during preparation (e.g., as an intermediate prior to injecting syringe contents into another receptacle) or may be used as administration receptacles into which substances are drawn. In any regard, pharmacies may produce large quantities of syringes for use in administration of medical care.

As such, prior approaches have been proposed that include automated syringe fillers that allow for automation of syringe filling. These approaches have ranged widely in specific approaches used to fill a syringe. These proposed approaches to automated syringe filling often rely on volumetric or gravimetric analysis to determine an amount of fluid that is drawn into a syringe. Also, such automated approaches often required predefined syringe characteristics for handling, filling, or other processing in the automated filler. In this regard, the applicability of the syringe fillers may be limited. For instance, prior approaches to automated syringe filling may be limited with respect to the nature of syringes that may be used with a given filler such that only a given size, type, or syringes manufactured by a given provider may be used in the filler. Accordingly, while automated syringe filling may provide advantages over manual preparation of syringes (e.g., increased efficiency, higher throughput, more accuracy, etc.), such devices continue to have limitations that inhibit their usefulness.

SUMMARY

The present disclosure generally relates to use of a vision system to measure syringe graduation marks. Specifically, the present disclosure facilitates use of a vision system in connection with a variety of different syringes that may differ with respect to size, type, manufacturer, configuration, or other characteristic. That is, the vision system may be adaptable to any number of different syringes to return accurate measurement of the pitch of graduation marks for a given syringe. This measurement may be, but need not be, used in conjunction with filling the syringe from which the graduated marks are measured. For instance, the vision system described herein may be used in other contexts where measurement of syringe graduation marks is desired such as, for example, for quality assurance purposes in syringe manufacturing or the like.

In this regard, the vision system described herein may be particularly suited for use in conjunction with a syringe filler (e.g., an automated syringe filler) to assist in determination of the pitch of graduation marks of a syringe to be filled using an automated syringe filler. In contrast to prior approaches of determining fill volumes for a syringe using volumetric or gravimetric calculations, use of the vision system as described herein to determine the pitch of graduation marks of a given syringe to be filled may allow the syringe to be filled based on and according to the graduation marks rather than based on volume or weight of fluid drawn into the syringe.

This may be beneficial in a number of respects. For instance, while volumetric and gravimetric approaches may provide high accuracy in connection with filling a syringe, the accuracy of the fill may not be visually determinable by a human handling the syringe. As may be appreciated, tolerances associated with the manufacturing of syringes may result in variation in the graduated marks on a syringe body. That is, when filling a syringe using a volumetric or gravimetric technique, the resulting syringe may still appear to be inappropriately filled as the syringe plunger may not precisely align with a corresponding graduated mark provided on the syringe that is reflective of the amount of fluid drawn into the syringe. Accordingly, a user handling the syringe (e.g., a nurse, physician, or other user administering the contents of the syringe) may view the syringe to be improperly filled given the discrepancy relative to the graduated marks provided on the syringe. Oftentimes such discrepancies lead to waste as a user may discard the syringe as being improperly filled based solely on the discrepancy of the contents of the syringe relative to the graduated marks.

However, by utilizing a vision system as contemplated herein to determine a pitch of the graduated markings on the syringe, an automated syringe filler may be used to fill the syringe based on the particular graduated markings provided on the given syringe to be filled. In this regard, the syringe may be accurately filled according to the given graduated marks for a syringe, and in turn, human users later handling the syringe may be able to verify the amount of liquid in the syringe by viewing the graduated marks. Use of the vision system may allow a syringe to be filled based on and according to the graduated marks in an automated manner. In turn, each syringe may be filled in a human verifiable manner. This may reduce waste as syringes filled using the vision system to measure the pitch of the graduated marks may not be judged to be inaccurately filled by a human user.

The vision system described herein may be used in other contexts beyond those described above without limitation. That is, the concepts described herein may be used to determine a pitch of any regular pattern on any object of interest. However, specific examples are described herein that involve use of the vision system to measure a pitch of graduated marks provided on a syringe body. In this regard, the vision system may be used to determine the distance between adjacent graduated marks. In combination with a known or measured diameter of the syringe, a volume for each graduated mark may be determined. As such, an automated syringe filler may use the known pitch of the syringe in combination with the volume for each graduated mark in filling a syringe. In turn, the syringe may be filled based on the graduated marks measured by the vision system for the given syringe such that the volume of liquid in the syringe corresponds to the graduated marks of the syringe. While the system described herein may be used in conjunction with a syringe filler (e.g., an automated syringe filler), it may also be provided as a stand alone measurement system that simply outputs information related to the pitch of the graduated marks as measured (e.g., for other contexts where measurement of the pitch is desired).

Accordingly, a first aspect includes a vision system for measurement of a pitch of a plurality of graduated marks on a syringe. The system includes an optical sensor having a field of view throughout which the optical sensor is operative to generate image data (e.g., digital image data). The system also includes a fixture engageable with a syringe to locate a syringe body of the syringe on a predetermined axis at an imaging position relative to the optical sensor. Accordingly, a plurality of graduated marks on the syringe body are disposable within the field of view of the optical sensor. The image data comprises measurement area data corresponding to at least one row of pixels extending perpendicularly to the direction in which each given one of the graduated marks extends on the syringe body. The system also includes a processing module, executed on a processor of the vision system, configured to process the measurement area data corresponding to the syringe to transform the measurement area data into a frequency domain representation of the measurement area data for the syringe (e.g., using a Fourier transform or the like). The frequency domain representation of the measurement area data is indicative of a fundamental frequency of the measurement area data for the syringe. In turn, the processing module is configured to determine the pitch of the plurality of graduated marks on the syringe body based on a known correspondence (e.g., a mathematical relationship) between the fundamental frequency of the measurement area data for the syringe and the pitch of the graduated marks on the syringe body.

A number of feature refinements and additional features are applicable to the first aspect. These feature refinements and additional features may be used individually or in any combination. As such, each of the following features that will be discussed may be, but are not required to be, used with any other feature or combination of features of the first aspect.

For example, in an embodiment the processing module may be configured to transform the measurement area data into the frequency domain using a discrete Fourier transform (DFT). The DFT may provide for efficient processing of the frequency domain representation of the measurement area data with relatively low processing resources. However, use of a DFT on limited length source signal (e.g., representing the limited measurement area used for pitch measurement) limits the resolution of the data in the frequency domain. Specifically, the resolution of the DFT is inversely proportional to the length of the source signal expressed in the units of the sample data (e.g., pixels in the examples described herein). In turn, the system may also include an interpolation module, executed on a processor of the vision system, configured to determine the fundamental frequency for a data set in the frequency domain using an interpolation of the resulting DFT on plurality of frequency domain data points in the frequency domain. Specifically, the plurality of frequency domain data points may include a maximum amplitude frequency data point and a first adjacent data point of higher frequency than the maximum amplitude frequency data point and a second adjacent data point of lower frequency than the maximum amplitude frequency data point. The interpolation module may be configured to apply a parabolic interpolation function to the plurality of frequency domain data points and solve for a maximum of the parabolic interpolation function corresponding to the fundamental frequency. However, other interpolation or curve fitting techniques may be applied to the frequency domain data points to interpolate a maximum corresponding to the fundamental frequency in view of the limited resolution of the DFT data points.

Also, use of a DFT may result in specific leakage distortions associated with the random nature of the beginning and ending values of the source signal within the area used for analyses. In turn, in an embodiment the vision system may include a windowing module to generate windowed measurement area data that may reduce or eliminate leakage distortions from the resulting frequency domain representation of the measurement area data. Specifically, the windowing module, executed on a processor of the vision system, may be configured to apply a window function to the measurement area data to generate windowed measurement area data used to transform the measurement area data into the frequency domain. The windowing function may convert source data so that beginning and finishing values of the source data set become equal to each other. Accordingly, anomalies regarding the discrete beginning and end of the sampled data set are reduced or eliminated. In this regard, a correctly selected window function may not notably affect the fundamental frequency of the measurement area data and may result in reduction or elimination of leakage distortions in the windowed measurement area data.

Further still, it may be advantageous to calibrate the vision system to reduce or eliminate optical distortions resulting from lens imperfections and variable geometries of the syringe to be measured relative to the optical sensor. Specifically, the optical sensor may be a relatively inexpensive and low-complexity sensor that lacks advanced optics or focusing mechanisms or the like. Also, a variety of syringe geometries may result in changes in the distance between the optical sensor and object to be measured. Therefore, the scale of the image on the sensor may differ for these various syringe geometries. In turn, calibration may use signal processing techniques to reduce or eliminate the influence on the measurement result of such geometrical or other optical distortions from the vision system. Furthermore, in an embodiment, the measurement area data corresponds to a measurement area offset along the predetermined axis from an image center of the field of view. This may reduce effects of glare or other optical distortions near the center of the field of view.

In relation to calibration of the vision system, an embodiment of the vision system may include a first calibration pattern having a plurality of calibration marks spaced at a first known (e.g., stored) calibration pitch. The first calibration pattern may be disposable in the imaging position relative to the optical sensor such that the measurement area data corresponds to at least one row of pixels extending perpendicularly to the direction in which each given one of the calibration marks extend. For example, the calibration pattern may be manually placed in the imaging position or may be moved into place automatically using a moveable component (e.g., the fixture) of the vision system. The vision system may also include a calibration module, executed on a processor of the vision system, that may be configured to process the measurement area data for the first calibration pattern to transform the measurement area data into a frequency domain representation of the measurement area data for the first calibration pattern that is indicative of a first calibration frequency of the measurement area data for the first calibration pattern corresponding to the first known calibration pitch. In turn, the processing module may be configured to determine the pitch of the plurality of graduated marks on the syringe using a function at least in part based on the fundamental frequency of the measurement area data for the syringe, the first known calibration pitch, and the first calibration frequency.

In another embodiment, the vision system may include a second calibration pattern having a plurality of calibration marks spaced at a second known calibration pitch. The second calibration pattern may be disposable in the imaging position relative to the optical sensor such that the measurement area data corresponds to at least one row of pixels extending perpendicularly to the direction in which each given one of the calibration marks extend. For instance, the second calibration pattern may also be manually or automatically moved into the imaging position. In an embodiment, the first and second calibration patterns may be provided on a common calibration block that bears both calibration patterns and which is moveable to place either calibration pattern in the imaging position. The calibration module may be configured to process the measurement area data for the second calibration pattern to transform the measurement area data into a frequency domain representation of the measurement area data for the second calibration pattern that is indicative of a second calibration frequency of the measurement area data for the second calibration pattern corresponding to the second known calibration pitch. In turn, the processing module may be configured to determine the pitch of the plurality of graduated marks on the syringe using a function at least in part based on the fundamental frequency of the measurement area data for the syringe, the first known calibration pitch, the second known calibration pitch, the first calibration frequency, and the second calibration frequency. In an embodiment of the vision system, the first calibration pitch and the second calibration pitch may be a common calibration pitch.

Furthermore, the calibration patterns may be disposed at different distances from the optical sensor to calibrate the system for all possible positions of the graduated marks of varying syringes relative to the optical sensor. As such, the first calibration pattern may be a first distance from the optical sensor and the second calibration pattern may be a second distance from the optical sensor and the plurality of graduated marks on the syringe may be a third distance between the first distance and the second distance from the optical sensor. Accordingly, the processing module may be configured to determine the pitch of the plurality of graduated marks on the syringe using a function at least in part based on the fundamental frequency of the measurement area data for the syringe, the common calibration pitch, the first calibration frequency, the second calibration frequency, the first distance, and the second distance.

In an embodiment, the vision system may be operative to determine when the graduated marks on a syringe are within the field of view such that the visions system may measure the pitch of the graduated marks in a manner described herein. In turn, the vision system may also have the capability to change the rotational orientation of the syringe about the predetermined axis to determine when the syringe is properly oriented such that the graduated marks appear in the measurement area. Specifically, in an embodiment, the fixture includes a syringe gripping apparatus that includes a plurality of gripping members. The gripping members may be disposed to engage, at a corresponding plurality of circumferentially offset locations, a syringe located at an axially aligned position on the predetermined axis. Each of the plurality of gripping members may include a corresponding roller for rotation about a longitudinal axis of the roller. The longitudinal axes of the rollers of the plurality of gripping members may be disposed parallel to each other and to the predetermined axis when the rollers are engaged with a syringe located at an axially aligned position on the predetermined axis. The system may also include an actuator for driven rotation of at least one of the rollers of the plurality of gripping members. Accordingly, upon the driven rotation each of the rollers co-rotate when the rollers are engaged with a syringe body located at an axially aligned position on the predetermined axis to rotate a syringe body located at an axially aligned position on the predetermined axis about the predetermined axis into a plurality of rotational orientations relative to the predetermined axis.

In connection with this type of fixture, the vision system may also include a control module, executed on a processor of the vision system, configured for control of the actuator. As such, the control module may be configured to control the actuator to rotate the syringe body about the predetermined axis such that the optical sensor captures a plurality of frames of measurement area data each corresponding to a different respective rotational orientation of the syringe about the predetermined axis. Specifically, the processing module may be configured to determine an amplitude of the fundamental frequency of the measurement area data for the plurality of frames of measurement area. When the amplitude of the first maximum of the DFT (which corresponds to the fundamental frequency of the measurement area data in the plurality of frames of measurement area data) exceeds a predetermined amplitude threshold, the syringe may be in an orientation such that the graduated marks are properly oriented relative to the optical sensor. Accordingly, the processing module may be in operative communication with the control module to cease rotation of the syringe about the predetermined axis when the fundamental frequency of the measurement area data in the plurality of frames exceeds the predetermined amplitude threshold. In an embodiment, the control module may cease rotation of the syringe about the predetermined axis when the fundamental frequency does not differ greater than a predetermined similarity threshold between two consecutive frames of the plurality of frames of measurement area data. In this regard, any contribution to the fundamental frequency other than graduated marks (e.g., text or other markings on the syringe) may be disregarded to the extend they contribute to a fundamental frequency that varies from frame to frame. The control module may be configured to control a speed of the rotation of the syringe about the predetermined axis based on a diameter of the syringe body.

In an embodiment, the measurement area data may comprise a single row of pixels extending along the graduated marks. However, in other embodiments, the measurement area data may comprise an aggregate (e.g., an average) of a plurality of pixel rows. For example, the fundamental frequency may be determined as an average of a plurality of fundamental frequencies calculated for a distinct plurality of rows of pixels extending perpendicularly to the direction in which each given one of the graduated marks extends on the syringe body. In another embodiment, the measurement area data may include an averaged row of pixels. Each pixel in the averaged row of pixels may include an average of the image data in a corresponding column of pixels of the measurement area data corresponding to a plurality of pixel rows extending perpendicularly to the direction in which each given one of the graduated marks extends on the syringe body. In turn, a single frequency domain representation of the averaged row of pixels may be generated to determine the fundamental frequency.

As discussed briefly above, a vision system as described herein may be utilized to measure the pitch of graduated marks on a syringe in a variety of contexts. One particular context may be use in connection with an automated syringe filling application. In this regard, the vision system may include a volume determination module, executed on a processor of the vision system, that may be configured to determine a calculated volume of the syringe per one graduated mark based on the pitch of the plurality of graduated marks on the syringe body and a diameter of the syringe body. The volume determination module may be configured to compare the calculated volume of the syringe per one graduated mark to a plurality of standard volumes to determine a standard volume to which the calculated volume corresponds (e.g., to which the calculated volume is the closest). The volume determination module may also be configured to determine a fill distance for linear travel of a syringe plunger of the syringe based on a requested fill volume divided by the standard volume multiplied by the pitch of the plurality of graduated marks on the syringe body. Furthermore, the volume determination module may be configured to fill check by comparing the fill distance to a syringe length to determine if the fill distance exceeds the syringe length.

Various embodiments may comprise any number of combinations of apparatus and/or method features described above and/or hereinbelow. Such combinations may include those encompassed by the following Embodiments:

1. A vision system for measurement of a pitch of a plurality of graduated marks on a syringe, comprising:
   an optical sensor having a field of view throughout which the optical sensor is operative to generate image data;
   a fixture engageable with a syringe to locate a syringe body of the syringe on a predetermined axis at an imaging position relative to the optical sensor such that a plurality of graduated marks on the syringe body are disposable within the field of view of the optical sensor, wherein the image data comprises measurement area data corresponding to at least one row of pixels extending perpendicularly to the direction in which each given one of the graduated marks extends on the syringe body; and
   a processing module, executed on a processor of the vision system, configured to process the measurement area data corresponding to the syringe to transform the measurement area data into a frequency domain representation of the measurement area data for the syringe that is indicative of a fundamental frequency of the measurement area data for the syringe, wherein the processing module is configured to determine the pitch of the plurality of graduated marks on the syringe body based on a known correspondence between the fundamental frequency of the measurement area data for the syringe and the pitch of the graduated marks on the syringe body.

2. The vision system of Embodiment 1, wherein the processing module is configured to transform the measurement area data into the frequency domain using a discrete Fourier transform (DFT), and the system further comprises:
   an interpolation module, executed on a processor of the vision system, configured to interpolate the fundamental frequency using a plurality of frequency domain data points in the frequency domain.

3. The vision system of Embodiment 1 or 2, wherein the plurality of frequency domain data points comprises a maximum amplitude frequency data point and a first adjacent data point of higher frequency than the maximum amplitude frequency data point and a second adjacent data point of lower frequency than the maximum amplitude frequency data point.

4. The vision system of any one of the Embodiments 1-3, wherein the interpolation module is configured to apply a parabolic interpolation function to the plurality of frequency domain data points and solve for a maximum of the parabolic interpolation function corresponding to the fundamental frequency.

5. The vision system of any one of the Embodiments 1-4, further comprising:
   a windowing module, executed on a processor of the vision system, configured to apply a window function to the measurement area data to generate windowed measurement area data used to transform the measurement area data into the frequency domain, wherein the window function does not notably affect the fundamental frequency of the measurement area data and reduces leakage distortions in the windowed measurement area data.

6. The vision system of any one of the Embodiments 1-5, further comprising:
   a first calibration pattern having a plurality of calibration marks spaced at a first known calibration pitch, wherein the first calibration pattern is disposable in the imaging position relative to the optical sensor such that the measurement area data corresponds to at least one row of pixels extending perpendicularly to the direction in which each given one of the calibration marks extend; and
   a calibration module, executed on a processor of the vision system, configured to process the measurement area data for the first calibration pattern to transform the measurement area data into a frequency domain representation of the measurement area data for the first calibration pattern that is indicative of a first calibration frequency of the measurement area data for the first calibration pattern corresponding to the first known calibration pitch;

wherein the processing module is configured to determine the pitch of the plurality of graduated marks on the syringe using a function at least in part based on the fundamental frequency of the measurement area data for the syringe, the first known calibration pitch, and the first calibration frequency.

7. The vision system of any one of the Embodiments 1-6, further comprising:

a second calibration pattern having a plurality of calibration marks spaced at a second known calibration pitch, wherein the second calibration pattern is disposable in the imaging position relative to the optical sensor such that the measurement area data corresponds to at least one row of pixels extending perpendicularly to the direction in which each given one of the calibration marks extend; and wherein the calibration module is configured to process the measurement area data for the second calibration pattern to transform the measurement area data into a frequency domain representation of the measurement area data for the second calibration pattern that is indicative of a second calibration frequency of the measurement area data for the second calibration pattern corresponding to the second known calibration pitch;

wherein the processing module is configured to determine the pitch of the plurality of graduated marks on the syringe using a function at least in part based on the fundamental frequency of the measurement area data for the syringe, the first known calibration pitch, the second known calibration pitch, the first calibration frequency, and the second calibration frequency.

8. The vision system of any of one the Embodiments 1-7, wherein the first calibration pitch and the second calibration pitch comprise a common calibration pitch.

9. The vision system of any of one the Embodiments 1-8, wherein the first calibration pattern is a first distance from the optical sensor and the second calibration pattern is a second distance from the optical sensor and the plurality of graduated marks on the syringe are a third distance from the optical sensor.

10. The vision system of any one of the Embodiments 1-9, wherein the processing module is configured to determine the pitch of the plurality of graduated marks on the syringe using a function at least in part based on the fundamental frequency of the measurement area data for the syringe, the common calibration pitch, the first calibration frequency, the second calibration frequency, the first distance, and the second distance.

11. The vision system of any one of the Embodiments 1-10, wherein the fixture further comprises:

a syringe gripping apparatus, comprising:

a plurality of gripping members disposed to engage, at a corresponding plurality of circumferentially offset locations, a syringe located at an axially aligned position on the predetermined axis, wherein each of the plurality of gripping members comprises a corresponding roller for rotation about a longitudinal axis of the roller, wherein the longitudinal axes of the rollers of the plurality of gripping members are disposed parallel to each other and to the predetermined axis when the rollers are engaged with a syringe located at an axially aligned position on the predetermined axis, and an actuator for driven rotation of at least one of the rollers of the plurality of gripping members, wherein upon the driven rotation each of the rollers co-rotate when the rollers are engaged with a syringe body located at an axially aligned position on the predetermined axis to rotate a syringe body located at an axially aligned position on the predetermined axis about the predetermined axis into a plurality of rotational orientations relative to the predetermined axis, and a control module, executed on a processor of the vision system, configured for control of the actuator;

wherein the control module is configured to control the actuator to rotate the syringe body about the predetermined axis such that the optical sensor captures a plurality of frames of measurement area data each corresponding to a different respective rotational orientation of the syringe about the predetermined axis;

wherein the processing module is configured to determine an amplitude of the fundamental frequency of the measurement area data for the plurality of frames of measurement area and configured to determine when the amplitude of the fundamental frequency of the measurement area data in the plurality of frames of measurement area data exceeds a predetermined amplitude threshold;

wherein the processing module is in operative communication with the control module to cease rotation of the syringe about the predetermined axis when the fundamental frequency of the measurement area data in the plurality of frames exceeds the predetermined amplitude threshold.

12. The vision system of any one of the Embodiments 1-11, wherein the control module ceases rotation of the syringe about the predetermined axis when the fundamental frequencies for respective consecutive frames of measurement area data do not differ greater than a predetermined value between two consecutive frames of the plurality of frames of measurement area data.

13. The vision system of any one of the Embodiments 1-12, wherein the control module is configured to control a speed of the rotation of the syringe about the predetermined axis based on a diameter of the syringe body.

14. The vision system of any one of the Embodiments 1-13, wherein fundamental frequency is determined as an average of a plurality of rows of pixels extending perpendicularly to the direction in which each given one of the graduated marks extends on the syringe body.

15. The vision system of any one of the Embodiments 1-14, wherein the measurement area data comprises an averaged row of pixels, wherein each pixel in the averaged row of pixels comprises an average of the image data in a corresponding column of pixels of the measurement area data corresponding to a plurality of pixel rows extending perpendicularly to the direction in which each given one of the graduated marks extends on the syringe body, and wherein a single frequency domain representation of the averaged row of pixels is generated to determine the fundamental frequency.

16. The vision system of any one of the Embodiments 1-15, further comprising:

a volume determination module, executed on a processor of the vision system, configured to determine a calculated volume of the syringe per one graduated mark based on the pitch of the plurality of graduated marks on the syringe body and a diameter of the syringe body.

17. The vision system of any one of the Embodiments 1-16, wherein the volume determination module is configured to compare the calculated volume of the syringe per one graduated mark to a plurality of standard volumes to determine a standard volume to which the calculated volume corresponds.

18. The vision system of any one of the Embodiments 1-17, wherein the volume determination module is configured to determine a fill distance for linear travel of a syringe plunger of the syringe based on a requested fill volume divided by the standard volume multiplied by the pitch of the plurality of graduated marks on the syringe body.

19. The vision system of any one of the Embodiments 1-18, wherein the volume determination module is configured to fill check by comparing the fill distance to a syringe length to determine if the fill distance exceeds the syringe length.

20. The vision system of any one of the Embodiments 1-19, wherein the measurement area data corresponds to a measurement area offset along the predetermined axis from an image center of the field of view.

21. A method for measurement of a pitch of a plurality of graduated marks on a syringe, comprising:
engaging a syringe having a syringe body with a plurality of graduated marks, wherein the syringe is engaged along a predetermined axis at an imaging position relative to an optical sensor;
capturing image data corresponding to a measurement area of a field of view of the optical sensor to generate measurement area data corresponding to the measurement area, wherein the measurement area data corresponds to at least one row of pixels extending perpendicularly to the direction in which each given one of the graduated marks extends on the syringe body;
generating a frequency domain representation of the measurement area data by applying a Fourier transform to the measurement area data;
determining a fundamental frequency of the measurement area data; and
calculating a pitch of the plurality of graduated marks based on a known correspondence between the fundamental frequency of the measurement area data of the syringe and the pitch of the graduated marks on the syringe body.

BRIEF DESCRIPTION OF THE DRAWINGS

FIGS. 9A-9D depict an embodiment of a calibration system that may be used with a vision system as described herein with various elements of the calibration system in different positions in the figures, FIGS. 10A-10C depicts an embodiment of an approach for determining an orientation of a syringe engaged with a vision system to determine when the graduated marks of the syringe are in the field of view of the imaging system.

DETAILED DESCRIPTION

The following description is not intended to limit the invention to the forms disclosed herein. Consequently, variations and modifications commensurate with the following teachings, skill and knowledge of the relevant art, are within the scope of the present invention. The embodiments described herein are further intended to explain modes known of practicing the invention and to enable others skilled in the art to utilize the invention in such, or other embodiments and with various modifications required by the particular applications(s) or use(s) of the present invention.

Figure 1:
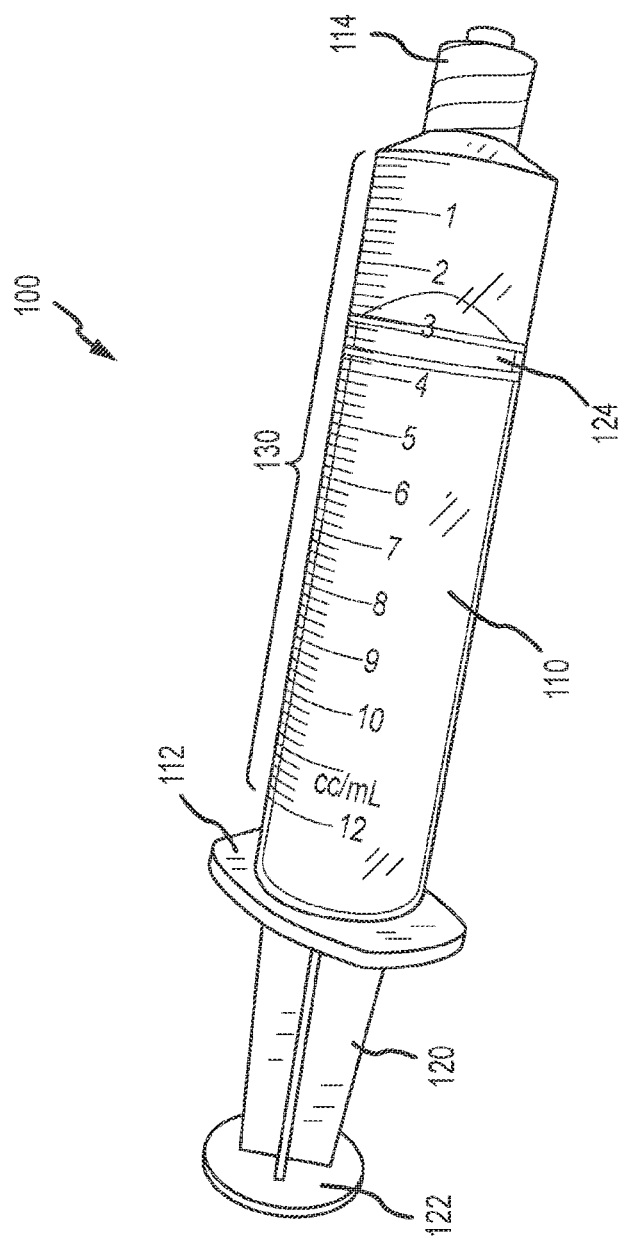
FIG. 1 depicts an embodiment of a syringe having graduated marks.

With reference to FIG. 1, an embodiment of a syringe 100 is shown. The syringe 100 may include a syringe body 110. The syringe body 110 may include a flange 112 and a port 114. In various embodiments, different configurations of ports 114 may be provided such as, for example, a slip luer connection, a threaded luer connection, or other appropriate port configurations. The syringe 100 may also include a plunger 120 that is displaceable relative to the syringe body 110. The plunger 120 may include a button 122 at a first end thereof and a seal 124 at an opposite end of the plunger 120. The seal 124 may seat against an inner wall of the syringe body 110. In turn, relative movement between the plunger 120 and the syringe body 110 may cause fluid to be drawn into the syringe body 110 through the port 114.

The syringe body 110 may include a plurality of graduated marks 130 arranged along the body 110 of the syringe 100. The graduated marks 130 may be calibrated relative to the syringe body 110 and plunger 120 such that the graduated marks 130 denote a volume of fluid drawn into the body 110 upon a given distance of relative movement between the syringe body 110 and the plunger 120. In this regard, the position of the seal 124 relative to the graduated marks 130 may indicate the amount of fluid contained in the syringe body 110. Each individual one of the graduated marks 130 may each extend circumferentially relative to the syringe body 110. In turn, the plurality of graduated marks 130 may collectively extend along the length of the syringe body 110 corresponding to the direction of relative movement between the syringe body 110 and the plunger 120. In turn, as the plunger 120 is retracted relative to the syringe body 110, the seal 124 may indicate, relative to the plurality of graduated marks 130, the volume of fluid in the syringe body 110. Accordingly, the plurality of graduated marks 130 may have a regular pitch (i.e., a regular distance between each adjacent graduated mark 130) to denote a given volume of the syringe body 110 between the graduated marks 130. The syringe 100 may also include a scale indicating the given volume denoted by the graduated marks 130.

During the manufacture of a syringe 100, the graduated marks 130 may be applied to the syringe body 110 using any number of appropriate processes. The application of the graduated marks 130 and/or other variations in the syringe manufacturing process may result in variances in the indicated volume of the graduated marks 130 from an absolute volume. That is, for a given indicated volume of fluid in the syringe 100, the actual volume of that fluid may vary from the indicated volume due to variances in the manufacturing process of the syringe 100. Accordingly, as described above, use of an absolute measure of volume when filling a syringe 100 without regard to the specific graduated marks 130 of a given syringe 100, as has been the traditional paradigm when automatically filling syringes, may result in the syringe 100 appearing to be inaccurately filled as the seal 124 may not align to the corresponding graduated mark 130 indicative of the fill volume. Accordingly, use of a vision system 150 as will be described herein may allow for variances in each syringe 100 to be determined for such that each syringe 100 may be filled to an appropriate corresponding graduate mark 130. As described above, this may allow for human verification of the volume in a syringe 100 even after the syringe 100 has been filled and leaves the pharmacy or other facility in which it is prepared.

Figure 2:
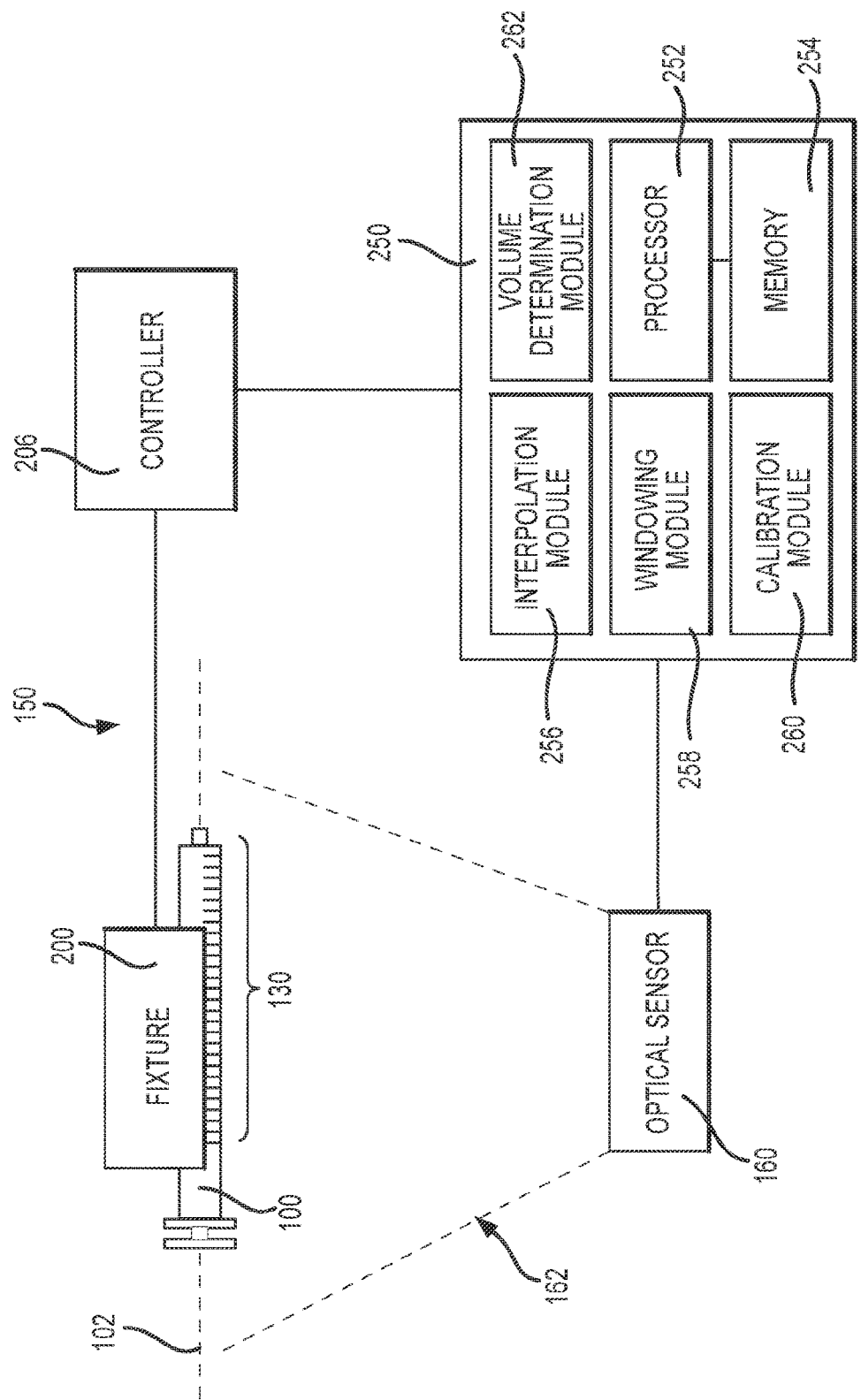
FIG. 2 depicts a schematic representation of an embodiment of a vision system.

With further reference to FIG. 2, a schematic view of an embodiment of a vision system 150 is shown. The vision system 150 may be operative to measure the pitch of graduated marks 130 on a syringe 100 engaged with the system 150. In this regard, the vision system 150 may include a fixture 200 that may engage a syringe 100. The fixture 200 locates the syringe 100 in an imaging position. The imaging position may be relative to a predetermined axis 102. That is, the syringe 100 may be engaged by the fixture 200 such that the syringe 100 is disposed along the predetermined axis 102. The predetermined axis 102 may be aligned with an optical sensor 160 such that the syringe 100 is disposed within a field of view 152 of the optical sensor 160 when in the imaging position. The fixture 200 may be fixed relative to the optical sensor 160. Alternatively, the fixture 200 may be moveable such that an engaged syringe 100 may be moved into the imaging position from a different position. The fixture 200 may include a syringe receiving portion in which a user may dispose a syringe 100 to be measured. Alternatively, the syringe receiving portion may be adapted to autonomously engage a syringe 100 without the intervention of a human user. The syringe receiving portion may be static or moveable to engage the syringe 100.

The optical sensor 160 may be operative to generate image data corresponding to the field of view 162. For example, the optical sensor 160 may be a digital imaging sensor capable of generating image data in the form of a plurality of pixel values for a plurality of pixels corresponding to the field of view 162 of the sensor. As will be utilized herein, a row of pixels may correspond to pixels extending along the length of the syringe 100 (i.e., from the button 122 to the port 114), whereas a column of pixels may correspond to pixels extending perpendicularly to the length of the syringe 100. The optical sensor 160 may, in an embodiment, be an 8-bit sensor capable of generating individual pixel values between 0 and 255, where the pixel value is a representation of the intensity of the image data for a given pixel. As such, a 0 value may correspond with a complete lack of intensity (i.e., a black pixel) and 255 may correspond to a complete intensity (i.e., a white pixel), with the range of pixel values representing various shades of gray between black and white. In this regard, the optical sensor 160 may be a single channel sensor capable only of generating pixel values representative of a single monochrome nature (i.e., a black and white sensor). In other embodiments, the optical sensor 160 may be a color sensor capable of generating intensity values for a plurality of channels representative of different colors.

The optical sensor 160 may be in operative communication with a processing module 250. In turn, the optical sensor 160 may provide generated image data from the field of view 162 to the processing module 250. The optical sensor 160 may provide constantly refreshed image data (i.e., a video stream) or may periodically provide, or provide on demand, image data for the field of view 162.

The processing module 250 may include a processor 252 (e.g., a physical computer processor device) in operative communication with a memory 254. In this regard, the processor 252 may be operative to access machine readable instructions comprising non-transitory machine readable data in the memory 254. The machine readable data stored in the memory 254 may be operative to specifically configure the processor 252 for performance of various functions described herein. As such, the processor 252 may be transformed from a general purpose computing processor to a specifically configured processor for accomplishing functionality related to various modules described herein upon access and execution of the data stored in the memory 254. For instance, various functionality is described herein as being executed by a processor of a module. Such modules may correspond to the processing module 250 generally or may relate to specific modules to be discussed in greater detail below. As may be appreciated, each module described herein may be an individual, discrete module having a corresponding processor 252 and memory 254 as described above where the memory 254 stores non-transitory machine readable data to configure the processor 252 to function as described in relation to a given module. Alternatively, multiple modules may be performed by a single processor 252 in communication with one or more physical memory devices comprising the memory 254. In this regard, the modules may correspond to different portions of non-transitory machine readable data stored in one or more physical memory devices. Further still, various ones or all of the modules may be executed using specifically configured hardware and/or software such as field programmable gate arrays, application specific integrated circuits, or the like. As such, the functionality of the various modules may be described herein in relation to functionality with the understanding that the functionality may be accomplished using any of the hardware, software, data, or techniques described herein.

Figure 3:
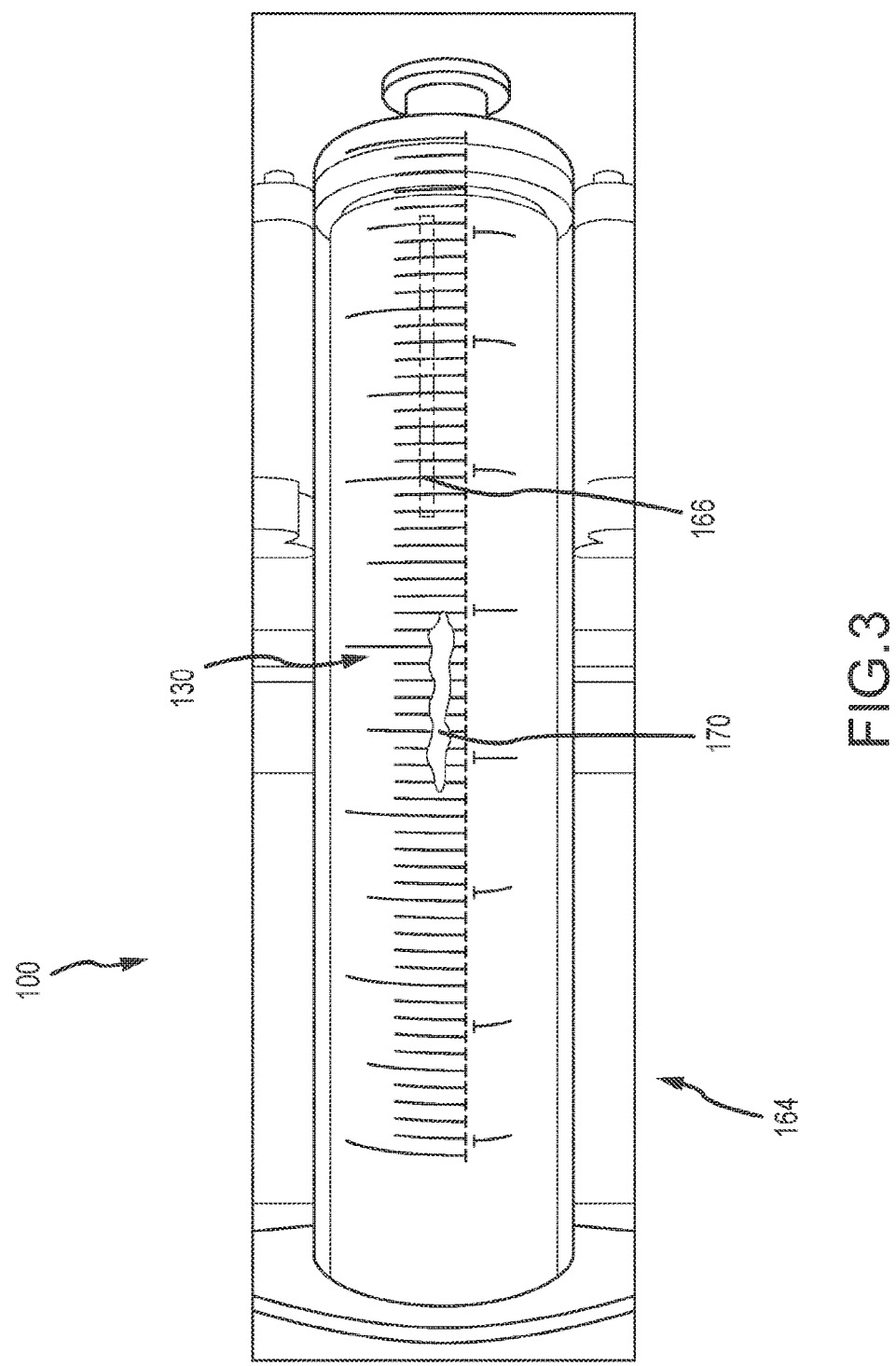
FIG. 3 depicts an embodiment of an image generated from a vision system.
Figure 4:
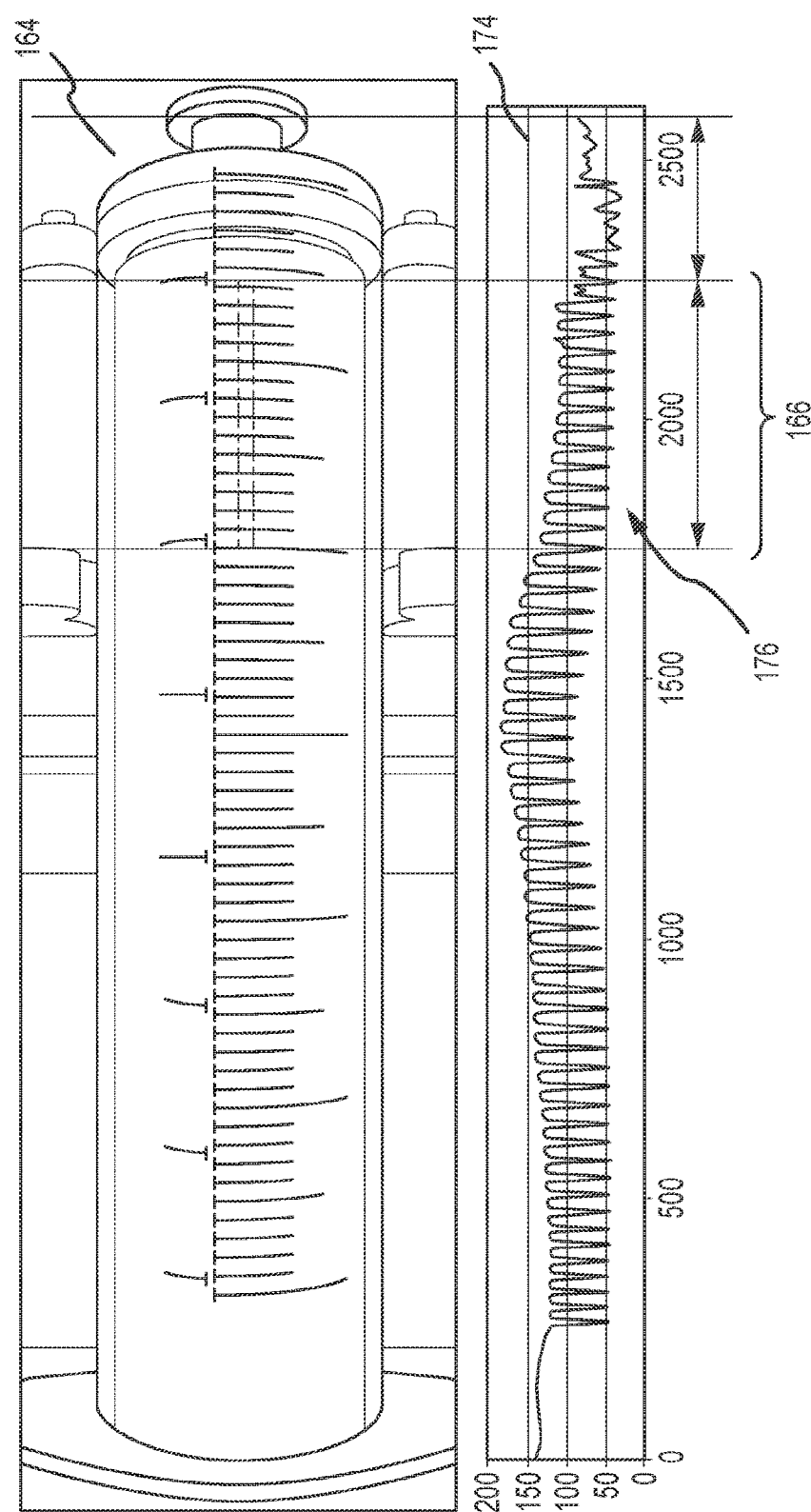
FIG. 4 depicts an embodiment of an image generated from a vision system in relation to a representation of image data from the image in the form of a plot of pixel intensity data.

In any regard, the processing module 250 may be operative to receive image data from the optical sensor 160. With further reference to FIG. 3, an image 164 corresponding to the image data of a field of view 162 of the optical sensor 160 is shown with a syringe 100 in the imaging position. A measurement area 166 is shown as an outlined subset of the image 164. The measurement area 166 may be a predefined portion of the image data of interest to be used in the measurement of the pitch of the graduated marks 130 of the syringe 100. With further reference to FIG. 4, an image 164 is shown juxtaposed in relation to a plot of the image data 174 for the image 164 corresponding to a row of pixels of the image data 164. As may be appreciated, the measurement area 166 is shown in relation to the image 164 and the data 174 and may represent the extent of the pixels from the measurement area 166.

The measurement area 166 may be offset from a side of the image 164 to account for imaging anomalies associated with, for example, the port 114 of the syringe 100, the seal 124 of the syringe 100, or other variations that may be present near the side of the image 164. That is, the measurement area 166 may be specifically defined so as to correspond to an area of a syringe 100 where the graduated marks 130 appear regardless of syringe type, size, manufacturer, or other syringe variation. In turn, a subset of the image data 174 for the measurement area 166 may be extracted from the image data 174. This may be referred to as measurement area data 176. In this regard, the measurement area data 176 taken from the image data corresponding to the image 164 may correspond to the graduated marks 130 of a syringe 100 disposed in the imaging position regardless of the specific syringe imaged. As such, the measurement area data 176 may comprise data for pixel values taken along the measurement area 166 that reflect the presence and absence of graduated marks 130. Furthermore, the length of the image data sample corresponding to the measurement area data 176 may correspond to an exponential of 2 to provide processing efficiency with realization of a DFT with algorithms referred to as Fast Fourier Transforms (FFT). For instance, the measurement area data 176 may include 512 values (i.e., corresponding with a length of 512 pixels in the image 164).

Figure 5:
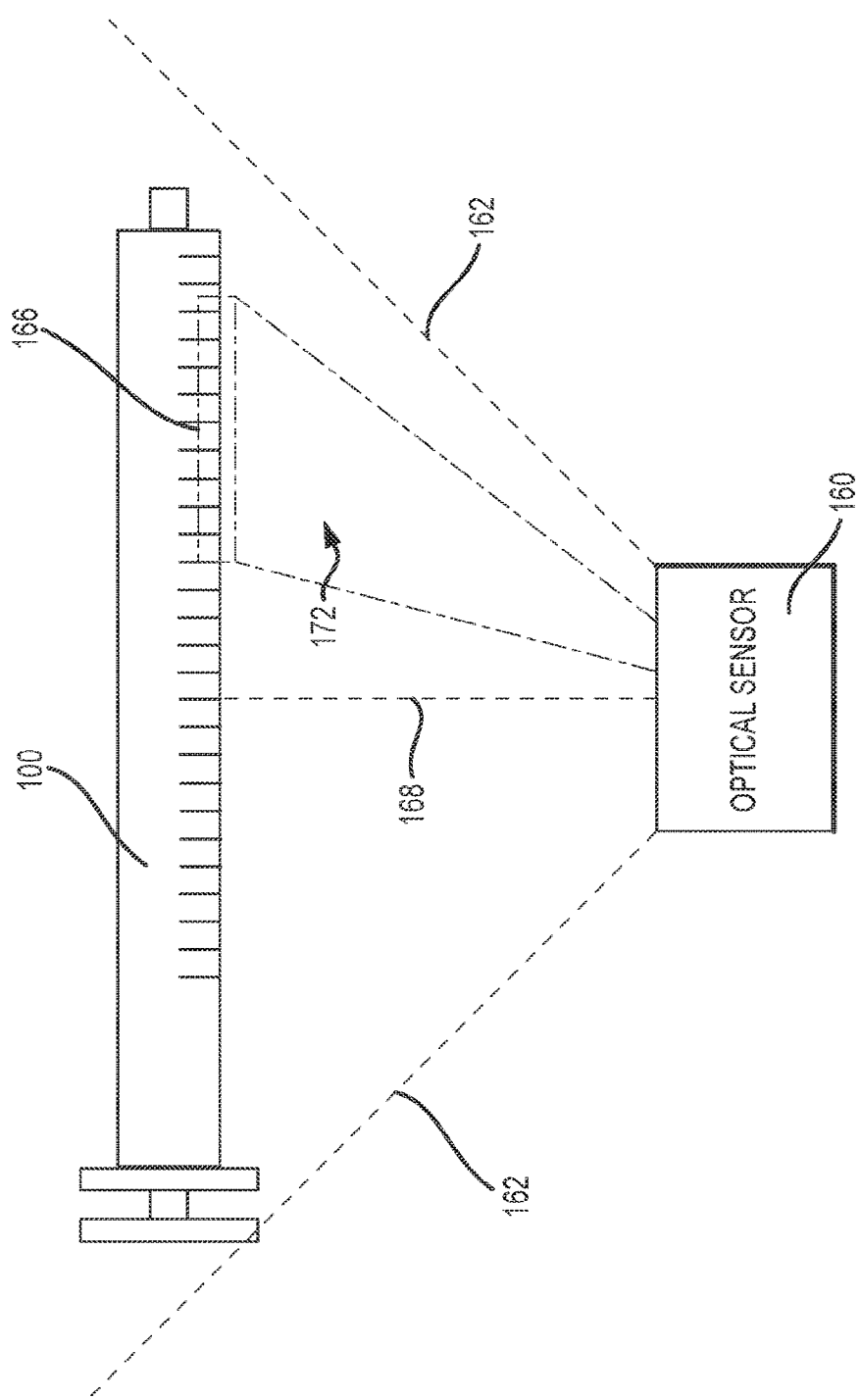
FIG. 5 depicts an embodiment of a field of view of the vision system in relation to a syringe positioned in relation thereto.

With further reference to FIG. 5, it may be appreciated that in addition to being offset from a peripheral edge of the field of view 162, the measurement area 166 may also be offset from a centerline 168 of the field of view 162. In this regard, the measurement area 166 may correspond to a subset 172 of the field of view 162. This may be to reduce effects of glare or other radiometric noise that may occur near the centerline 168 of the image data 174. For instance, as shown in FIG. 3, a pronounced area of glare 170 occurs in relation to the graduated marks 130 near the center of the image 164. In turn, the portion of the field of view 162 associated with the measurement area 166 may be offset from both a peripheral edge of the field of view 162 as well as from a centerline 168 of the field of view 162.

As best seen in FIG. 3, the measurement area 166 may correspond to at least one row of pixels that extends perpendicularly to the direction in which each given one of the graduated marks 130 extends on the syringe body 110. Accordingly, the processing module 250 may be operative to receive the measurement area data 176 corresponding to the measurement area 166. As shown in the plot 174, the measurement area data 176 may correspond to the image data (e.g., pixel intensity values between 0 and 255 for an 8-bit sensor) for the row of pixels that extends perpendicularly to the graduated marks 130. In this regard, the measurement area data 176 may reflect the graduated marks 130 as darkened areas in the image data 174 corresponding to image data reflecting the reduced pixel intensity.

As will be appreciated in the discussion below, a measurement technique to determine the pitch of the graduated marks 130 of a syringe 100 may be performed individually for a plurality of rows from the measurement area 166, with each row of pixels in the measurement area 166 representing a set of measurement area data 176. In turn, the results from each measurement may be averaged in arriving the pitch. Alternatively, a plurality of rows of pixels may be averaged to generate the measurement area data 176. In this regard, a column of pixels, each representing a given pixel from the row of the measurement area 166 may be averaged to determine an average pixel intensity value for that column of pixels. As such, the measurement area data 166 may comprise an average pixel row corresponding to the plurality of rows of pixels in the measurement area 166. For instance, 20 rows of pixels may be provided in the measurement area 166. As such, each value in the measurement area data 176 may represent an average pixel intensity for the column of pixels in a given pixel location across all rows of pixels. In this regard, the measurement area data 176 may correspond to the pixel intensity values of one or more rows of pixels taken along the measurement area 166. Accordingly, a single measurement of the averaged pixel data comprising the measurement area data 176 may be performed.

Figure 6:
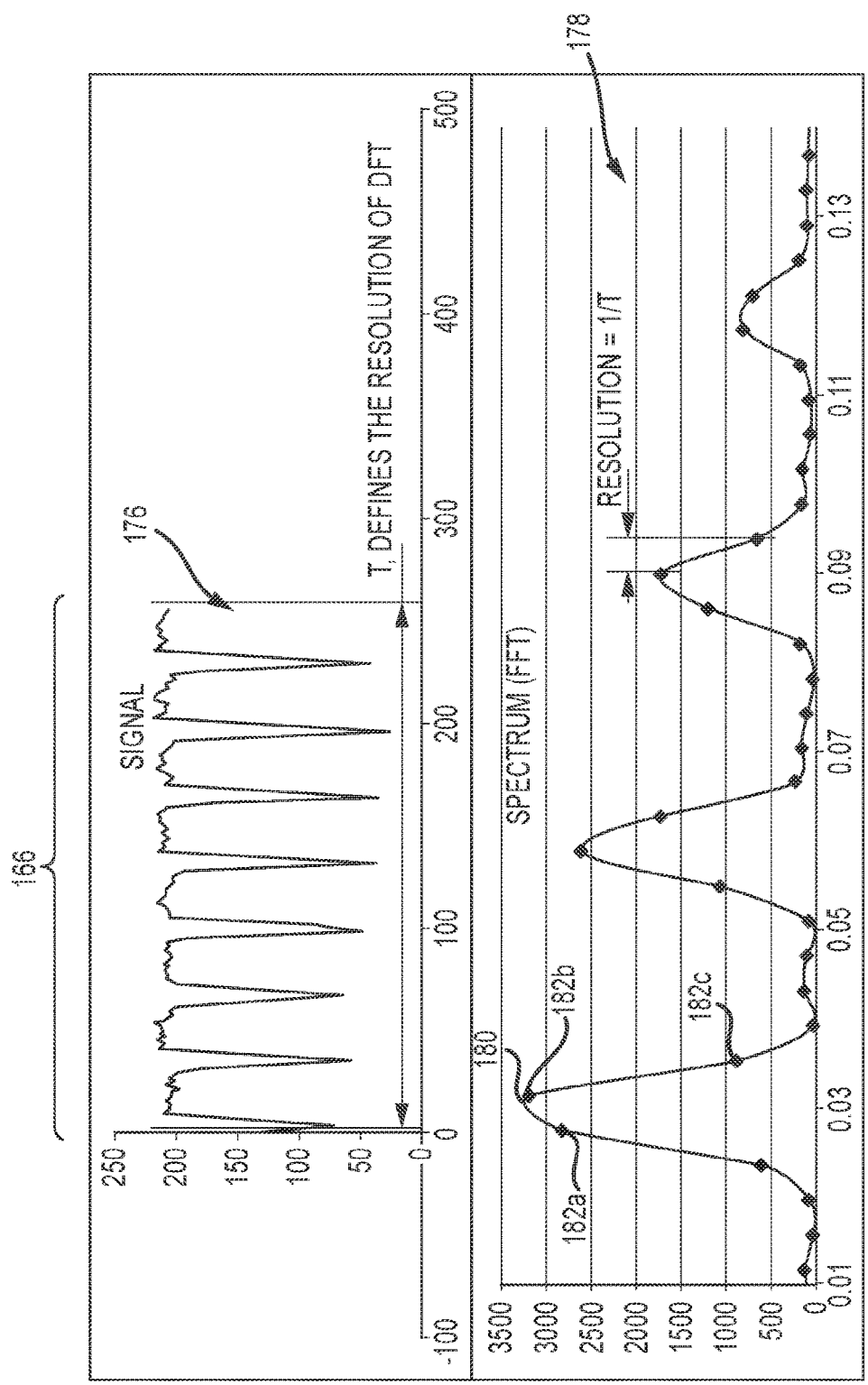
FIG. 6 depicts an embodiment of a plot of image data and a corresponding frequency domain plot corresponding to the image data.

In turn, and with further reference to FIG. 6, the processing module 250 may be operative to transform the measurement area data 176 into the frequency domain, which is represented by plot 178 where frequency is represented on the horizontal axis and amplitude is represented on the vertical axis. For example, the measurement area data 166 may be processed by the processing module 250 such that a Fourier transform of the measurement area data 166 may be calculated to represent the measurement area data 176 in the frequency domain. In turn, the measurement area data 166 may be represented in the frequency domain as shown in plot 178. As may be appreciated, the fundamental frequency 180 of the measurement area data 166 may be identified in the plot 178 as the frequency having the largest amplitude of the frequency domain plot 178.

The fundamental frequency 180 may have a known correspondence to the pitch of the plurality of graduated marks 130. For example, an inverse of the fundamental frequency 180 may correspond to the pitch of the graduated marks 130. As shown in FIG. 6, the fundamental frequency 180 may be at 0.03 corresponding to a pitch of 33 pixels between adjacent graduated marks 130. Accordingly, upon identification of the fundamental frequency 180 of the measurement area data 176 in the frequency domain, the pitch of the graduated marks 130 may be calculated by taking the inverse of the fundamental frequency 180.

The processing module 250 may be operative to apply a Fourier transform to the measurement area data 176. In an embodiment, this may be by applying a fast Fourier transform (FFT) to the measurement area data 176. In this regard, the FFT may comprise a discrete Fourier transform (DFT) of the measurement area data 176. As may be appreciated, the resolution of the representation of the measurement area data 176 in the frequency domain may be related to the sample size of the measurement area data 176. Specifically, the length of the measurement area data 176 (e.g., the number of pixels of image data in the measurement area data 176) may correspond to the resolution of the frequency domain plot 178. As the size of the measurement area data 175 may be limited, so may the resolution of the frequency domain plot 178 be limited. Specifically, a plurality of frequency domain data points 182 may be provided at a resolution in the frequency domain plot 178 corresponding to the inverse of the number of pixels of the measurement area data 176. As this resolution may be limited, the maximum frequency domain data point 182 associated with an indicated fundamental frequency 180 may include error associated with aliasing in the frequency domain plot 178.

In turn, an interpolation module 256 may be provided to interpolate the frequency domain data points 182 in the frequency domain to overcome any aliasing in the measurement area data 176. Specifically, the frequency domain data points 182a and 182c adjacent to the maximum data point 182b of the frequency domain 178 may be used to determine a more accurate measure of the fundamental frequency 180 using interpolation.

Figure 7:
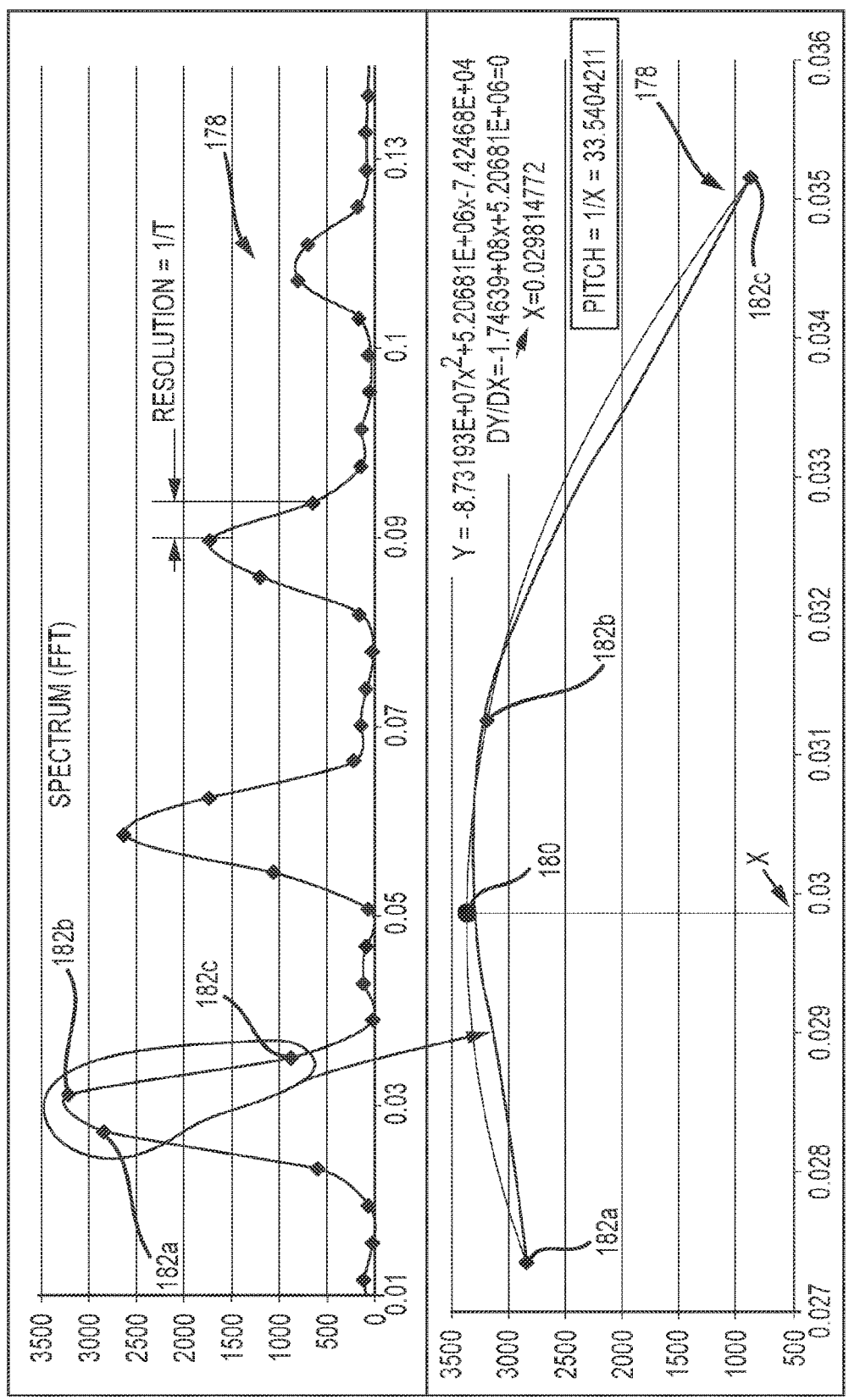
FIG. 7 depicts a detailed view of a frequency domain plot for a set of image data including details regarding an embodiment of a process for reduction or elimination of resolution limitations with DFT interpolation among three frequency domain data points surrounding the DFT maximum.

As shown in FIG. 7, an embodiment of a frequency domain plot 178 associated with measurement area data 176 is shown. The frequency domain plot 178 includes a plurality of frequency domain data points 182. In turn, the interpolation module 256 may be operative to identify a frequency domain data point 182b having a relative maximum amplitude in the frequency domain 178 relative to the other frequency domain data points 182. Additionally, the interpolation module 256 may identify an adjacent frequency domain data point 182a of lower frequency in the frequency domain plot 178 and an adjacent frequency domain data point 182c of higher frequency in the frequency domain plot 178. In turn, using the three frequency domain data points 182a, 182b, and 182c, the interpolation module 256 may be operative to use an appropriate interpolation technique to characterize the frequency domain data points 182a, 182b, and 182c. For example, a parabolic interpolation may be applied to the frequency domain data points 182 to arrive at a polynomial function that characterizes the data points 182. In alternative embodiments, other curve fitting techniques may be employed. Furthermore, higher order polynomial functions may be utilized. Further still, more than three frequency domain data points 182 may be used in the interpolation. However, it has been found that a parabolic interpolation provides good results while reducing computing overhead.

In turn, a maximum of the polynomial function that describes the frequency domain data points 182 may be found to determine a maximum of the function corresponding to the fundamental frequency 180 of the frequency domain 178. For instance, a derivative of the polynomial function may be equated to zero to solve for the fundamental frequency 180. In turn, the interpolation module 256 may provide the fundamental frequency 180 to the processing module 250 that may be used to determine the pitch of the graduated marks 130 as described above (e.g. by taking the inverse of the fundamental frequency 180).

Figure 8:
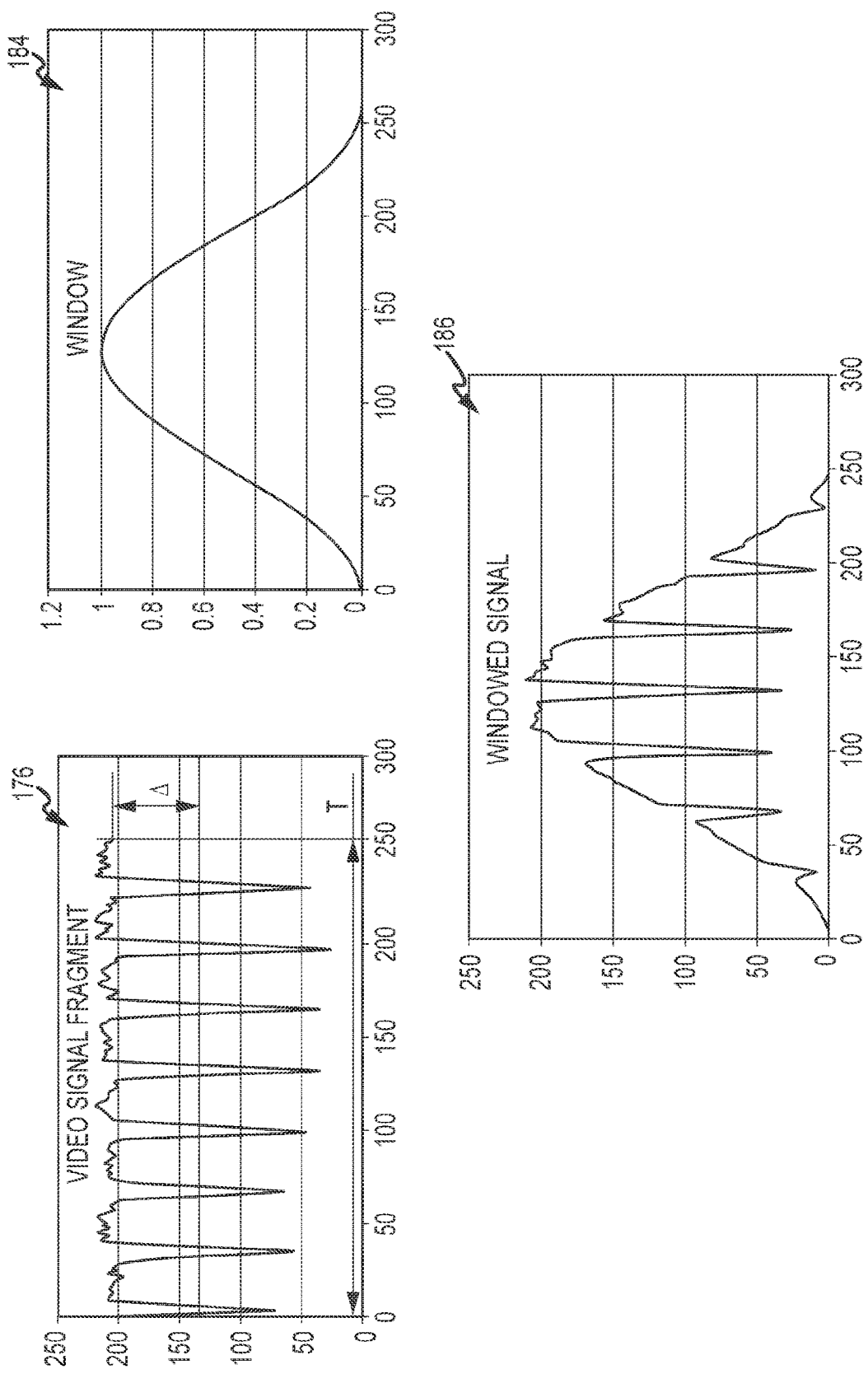
FIG. 8 depicts an embodiment of use of a windowing function applied to image data to achieve a windowed signal.

Furthermore, given the measurement area data 176 corresponds to a limited, discrete length of image data rather than an unlimited, continuous length function, when transforming the measurement area data 176 into the frequency domain, the represented data in the measurement area data 176 may be subject to leakage distortions. The main reason of these distortions is the random character of the beginning and finishing values of the data set 176, which is preferably equal to each other to avoid these distortions. Accordingly, the processing module 250 may include a windowing module 258. With further reference to FIG. 8, the windowing module 258 may be operative to apply a windowing function 184 to the measurement area data 176. This may result in a windowed signal 186. The windowed signal 186 may be used to transform the measurement area data 176 into the frequency domain as the windowed signal 186 may include all the frequency information of the measurement area data 176 without any distortions due to leakage resulting from different, random values of the first and the last elements of data set 176 associated with the measurement area 166.

Additionally, the measurement area data 176 may be subject to various distortions or other optical noise based on geometric and other distortions of the optical sensor 160. For instance, it may be advantageous to use a relatively simple optical sensor 160 to reduce complexity and/or cost of the vision system 150. For instance, the optical sensor may be a CCD sensor or other type of relatively simple optical sensor. As such, the optical sensor 160 may lack advanced optics elements (e.g., high precision lenses or the like) and therefore geometrical distortions of the lens in such sensor may be very high (e.g., with errors up to 10%-15% based on the geometrical distortions). Additionally, because the imaging system 150 may be used in conjunction with syringes 100 of various diameters, the precise distance and/or angle at which the graduated marks 130 are disposed relative to the optical sensor 160 upon capturing the image data may also differ from syringe to syringe. Specifically, because a syringe 100 may be located on a predetermined axis 102 relative to the optical sensor 160 the diameter of the syringe body 110 may result in the graduated marks 130 being disposed at different distances and/or angles relative to the optical sensor 160 when syringes 100 of different diameters are located on the predetermined axis 102 in the imaging position.

However, rather than providing an optical sensor 160 with costly and complex optics, it has been found that the geometric distortions of the optical sensor 160 may be reduced or eliminated with use of calibration. In this regard, a calibration module 260 may be provided to account for various noise or other optical distortions that may be present in the vision system 150 without the use of advanced optics such as precision lenses or focusing devices. Specifically, it has been found that the errors related to the optical distortions in the measurement area data 176 resulting in the physical geometry of the optical sensor 160 relative to an imaged syringe 100 may be linear relative to both the pitch to be measured and the distance between the optical sensor and object of interest. Accordingly, the calibration module 260 may be operative to generate a calibration function (e.g., a linear calibration function) that may be applied to account for any geometric distortions when calculating the pitch of the graduated marks 130.

Specifically, the calibration module 260 may be operative to apply a calibration function during the processing of measurement area data 176 based on calibration data obtained by the calibration module 260. With further reference to FIG. 9A-9D, an embodiment of a calibration system 350 that may be employed in conjunction with the calibration module 260 is shown. The calibration system 350 may include a calibration block 300 that may include one or more calibration patterns. For instance, a calibration pattern 302 of a known pitch may be placed relative to the optical sensor 160. The calibration pattern 302 may be printed or otherwise disposed on the calibration block 300 that may be moved into the imaging position relative to the optical sensor 160. For example, the calibration block 300 may be provided on the fixture 200, which may be movable relative to the optical sensor 160. Alternatively, the calibration block 300 may be separate from the fixture 200 and automatically or manually moved into the imaging position to obtain calibration data regarding the calibration pattern 302.

Figure 9B:
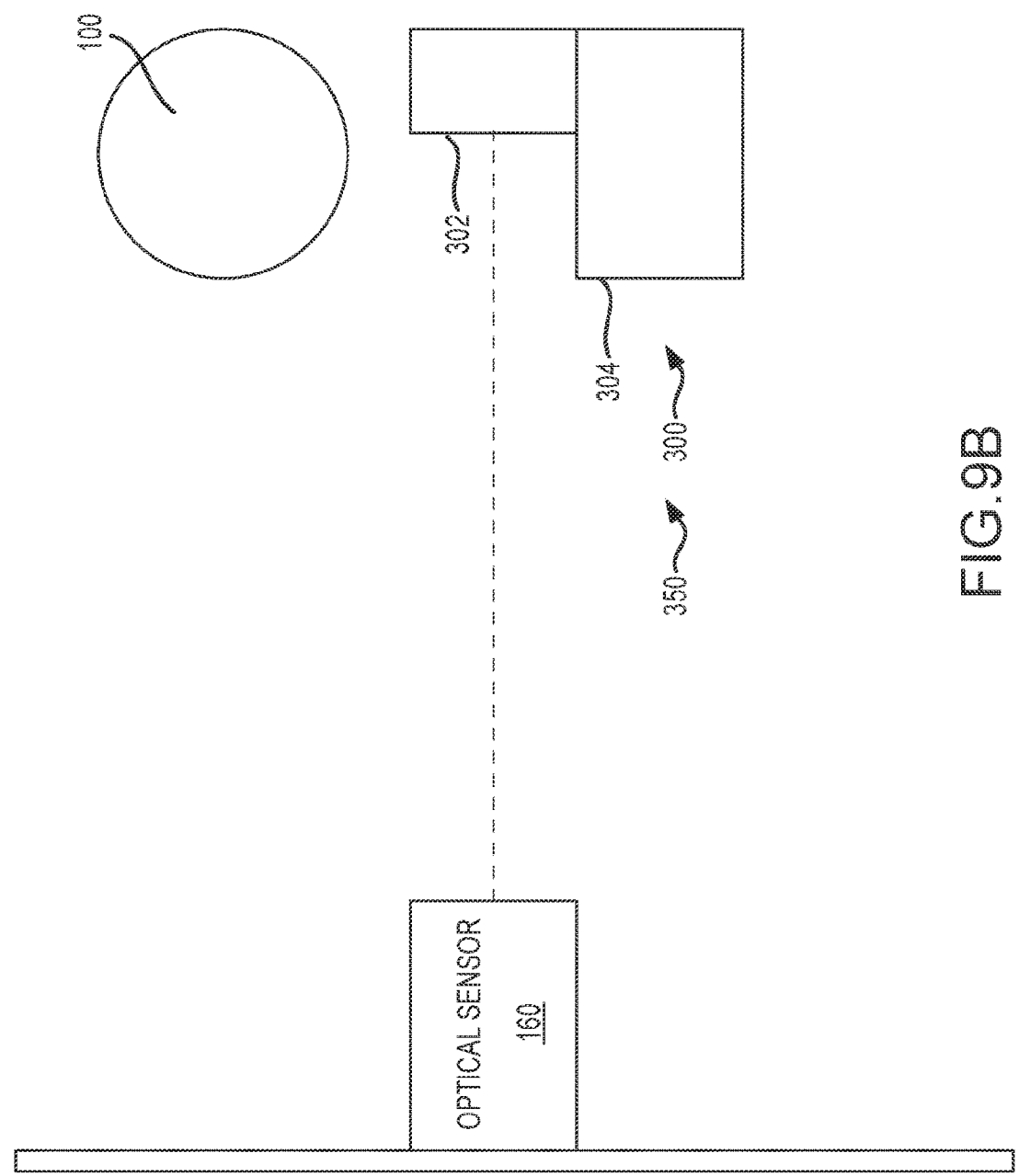

With reference to FIG. 9B, the calibration pattern 302 is in place in the imaging position. When in this position, the optical sensor 160 may be operative to capture image data from the measurement area 166 corresponding to the calibration pattern 302. That is, the same pixel area and/or averaging technique used to measure a syringe 100 may be used in relation to the calibration pattern 302. In turn, the calibration module 260 may be operative to calculate calibration data comprising a fundamental frequency of the measurement area data 176 corresponding to the calibration pattern 302 having a known pitch using a frequency domain representation of the measurement area data 176 for the calibration pattern 302 (e.g., using a technique as described above).

Figure 9C:
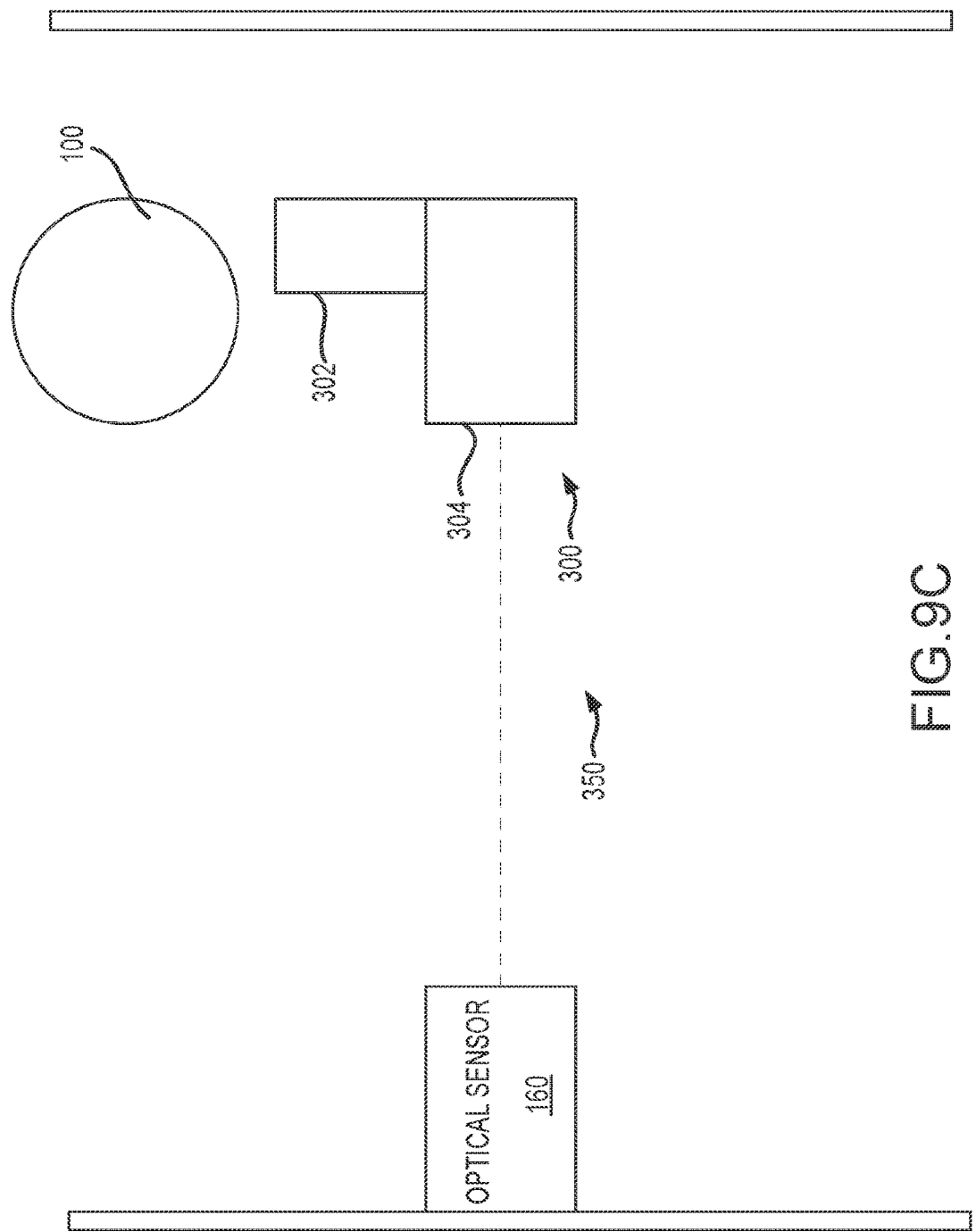

With further reference to FIG. 9C, the calibration block 300 may also include a second calibration pattern 304 that may be moved relative to the optical sensor 160 such that calibration pattern 304 is disposed in the imaging position relative to the optical sensor 160. The calibration pattern 302 and the calibration pattern 304 need not be placed on a common calibration block 300 as depicted. The optical sensor 160 may be operative to capture data from the measurement area 166 when the calibration pattern 304 is in the imaging position. The calibration module 260 may be further operative to generate calibration data comprising a fundamental frequency for the calibration pattern 304 having a known pitch using a frequency domain representation of the measurement area data 176 for the calibration pattern 304.

With reference to FIG. 9A, the predetermined axis 102 of the syringe 100 when the syringe 100 is in the imaging position (as shown in FIG. 9D), may be a first distance 306 from the optical sensor 160. The first calibration pattern 302 may be a second distance 308 from the optical sensor 160 and the second calibration pattern 304 may be a third distance 310 from the optical sensor 160. As may be appreciated, the second distance 308 may be, but is not required to be, greater than the first distance 306 and the third distance 310 may be, but is not required to be, less than the first distance 306. While the diameter 312 of the syringe 100 may vary depending on the particular syringe 100 to be imaged, in one embodiment the third distance 310 may be selected such that the calibration pattern 304 is placed nearer to the optical sensor 106 than any graduation mark appearing on any syringe body 110 used in the vision system 150. That is, the third distance 310 may be less than the first distance 306 reduced by half of any diameter 312 of any syringe 100 potentially used in the system 150. As may be appreciated from FIG. 9A, the second distance 308 may be greater than the first distance 306 such that the calibration pattern 302 is disposed at a distance beyond the predetermined axis 102 when the calibration pattern 302 is in the imaging position. However, the arrangement of the first and second calibration patterns 302 and 304 may be otherwise provided such that the second distance 308 and third distance 310 are different than the embodiment described herein and depicted in FIGS. 9A-9O.

As such, the calibration module 260 may be operative to utilize the calibration data gathered regarding the calibration patterns 302 and 304 and known characteristics regarding the calibration patterns 302 and 304 to provide a calibrated measure of the graduated marks 130 on a syringe 100 such that variations or optical distortions resulting from the geometry of the syringe 100 relative to the imaging device 160 are reduced or eliminated. For instance, the calibration module 260 may be operative to determine a calibrated pitch for a syringe 100 based on (e.g., using a function including) the fundamental frequency 180 of the measurement area data 176 measured for the syringe 100, a known calibration pitch for a given one of the calibration patterns 302 or 304, and a measured calibration frequency for the given one of the calibration patterns 302 or 304. As stated above, the calibration frequency for a calibration pattern may correspond to the fundamental frequency for the calibration pattern, which may be determined using the processing module 250 as described above in relation to use of a DFT (e.g., possibly using the interpolation module 256 and/or windowing module 258) as described above.

In an embodiment, both of the calibration patterns 302 and 304 may be utilized to provide a calibrated pitch measure for a syringe 100 to account for linear optical distortions due to the geometry of the vision system 150. The second distance 308 and the third distance 310 are known. Also, the distance between the syringe body 110 on which the graduation marks 130 appear and the optical sensor 160 may be also known through the known first distance 306 and diameter of the syringe 100 which may be a known input by a user or measured elsewhere and provided to the calibration module 260. As such, the fundamental frequency 180 for a syringe 100 may be calibrated using the first known calibration pitch of the first calibration pattern 302, the second known calibration pitch of the second calibration pattern 304, the calibration frequency of the first calibration pattern 302 as measured by the calibration module 260, the calibration frequency of the second calibration pattern 304 as measured by the calibration module 260, the second distance 308, and the third distance 310, to determine a calibrated pitch for the syringe 100. Specifically, this relationship is described with the equation:

$$P_x = P_c \frac{F_2 - \frac{\left(L_d + \frac{d}{2}\right)*(F_2 - F_1)}{(L_c)}}{F_x} \qquad \text{Equation 1}$$

In Equation 1, $P_x$ is the calibrated pitch for a syringe, $P_c$ is the known calibration pitch (which may be the same for both calibration patterns 302 and 304 for simplicity), $L_d$ is the difference between the second distance 308 and the first distance 306, d is the diameter of the syringe 100 (which may be a known input by a user or measured elsewhere and provided to the calibration module 260), $F_1$ is the measured calibration frequency of the first calibration pattern 302, $F_2$ is the measured calibration frequency of the second calibration pattern 304, $L_c$ is the difference between the second distance 308 and the third distance 310, and $F_x$ is the fundamental frequency 180 for the graduated marks 130 of the syringe 100 being measured (e.g., as determined using the FFT processing described above). As stated above, the first known calibration pitch and second known calibration pitch may be the same to simplify the calculation of the calibrated pitch. Furthermore, the measurement of the first calibration frequency and the second calibration frequency need not be performed for every syringe 100 measured. For instance, these calibration frequencies may be calculated periodically (e.g., upon initialization of the vision system 150) and stored in the memory 254 for use with a plurality of syringes 100.

With returned reference to FIG. 2, a syringe 100 may be engaged with a fixture 200 for positioning of the syringe 100 in the imaging position relative to the optical sensor 160. The graduated marks 130 appearing on the syringe 100 may be disposed such that the graduated marks 130 are visible in the field of view 162 of the optical sensor 160. The fixture 200 may be configured such that the fixture 200 engages the syringe 100 such that the graduated marks 130 are arranged in the field of view 162 of the optical sensor 160. Alternatively, the fixture 200 may be configured to allow for the fixture 200 to orient the syringe 100 relative to the optical sensor 160 such that the graduated marks 130 are oriented in the field of view 162. In this later regard, the processing module 250 may monitor measurement area data 176 during orientation of the syringe 100 to determine when the graduated marks 130 are disposed in the imaging field 162.

With additional reference to FIGS. 10A-10C and 11, an embodiment of a fixture 200 is shown for engaging a syringe 100. The fixture 200 may include a syringe gripping apparatus comprising a plurality of gripping members 202. The gripping members 202 may engage the syringe 100 at a corresponding plurality of circumferentially offset locations. As shown best in FIG. 11, the gripping members 202 may comprise rollers for rotation about a longitudinal axis of each one of the rollers. The longitudinal axis of each of the rollers may be parallel to each other and to the predetermined axis 102 on which the syringe 100 may be axially aligned. Additionally, an actuator (not shown) may be engaged with one or more of the gripping members 202. The actuator may be operative to rotate one or more of the gripping members 202. For instance, the rollers may be rotated about a longitudinal axis by the actuator. Upon rotation of the one or more gripping members 202, the syringe 100 may also be rotated about the predetermined axis 102. This may allow for the syringe 100 to be disposed into different rotational orientations relative to the predetermined axis 102.

Figure 11:
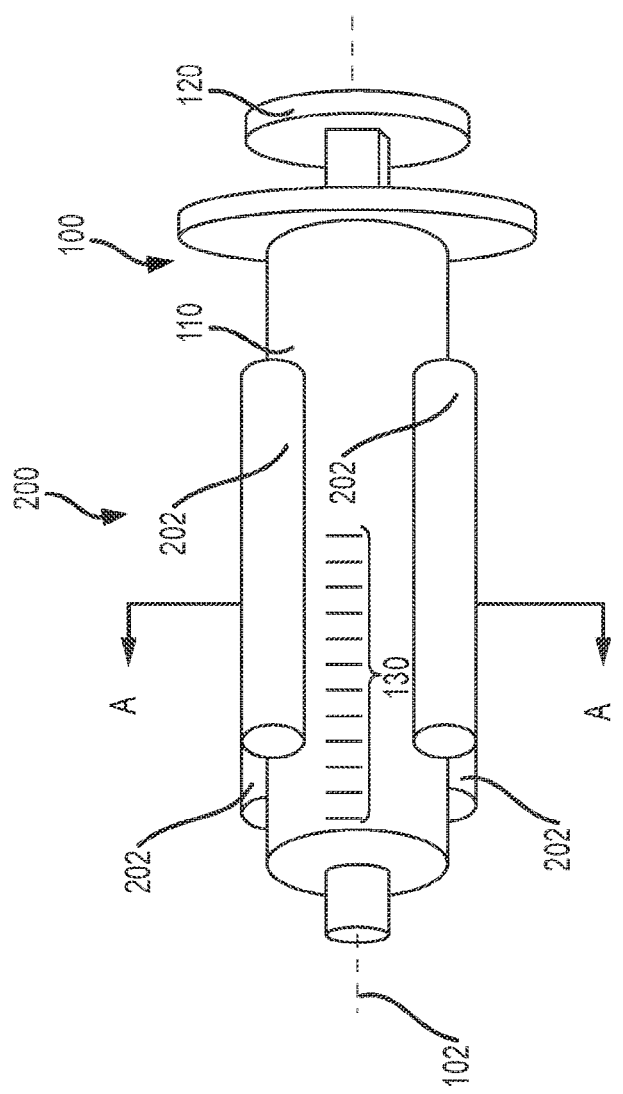
FIG. 11 depicts a perspective view of a syringe engaged with a fixture capable of modifying the rotational orientation of the syringe relative to a predetermined axis.

With further reference to FIGS. 10A-10C, a cross sectional view of the syringe 100 taken along section line A-A in FIG. 11 is shown in the upper portion of FIGS. 10A-10C. As may be appreciated, the graduated marks 130 are represented along the syringe body 110 of the syringe 100 as a darkened portion of the syringe body 110. In FIG. 10A, the graduated marks 130 may face away from the optical sensor 160. In this regard, a frequency domain plot 178 of the frequency domain representation of measurement area data 176 for the syringe 100 in FIG. 10A may not have any predominant frequencies. That is, a threshold amplitude 204 may be established. The amplitude threshold 204 may be a predetermined value. For instance, the amplitude threshold 204 may be a predetermined value based on the diameter of the syringe 100 and/or the maximum value of the pixels within measurement area data 176.

In any regard, the fixture 200 may be in operative communication with a controller 206 as shown in FIG. 2. The processing module 250 may command the controller 206 to initiate rotation of the syringe 100 about the predetermined axis 102. In an embodiment, the speed of rotation of the syringe 100 imparted by the gripping member(s) 202 may be based on a diameter of the syringe 100. The diameter 100 may be known (e.g., provided by a user or another system) measured. In turn, the actuator may drive one or more of the gripping members 202 to initiate rotation of the syringe 100 to move the syringe to a different rotational orientation as described above.

During such rotation of the syringe 100, the processing module 250 may be operative to continue to determine a frequency domain representation 178 of the measurement area data 176 taken for the syringe 100. As can be appreciated in FIG. 10B, the syringe 100 may be in a second rotational orientation such that a portion of the graduated marks 130 may appear in the field of view 162 of the optical sensor 160. Accordingly, the frequency domain plot 178 may show some frequency information. However, none of the frequencies represented in the frequency domain plot 178 may exceed the threshold amplitude 204. Accordingly, the controller 206 may continue to control the actuator to continue rotation of the syringe 100.

Specifically, the controller 206 may continue to rotate the syringe 100 until the amplitude of a frequency in the frequency domain plot 178 exceeds the amplitude threshold 204 as shown in FIG. 10C. Once the amplitude threshold 204 has been exceeded by a frequency in the frequency domain plot 178, the controller 206 may discontinue rotation of the syringe 100. The amplitude of a frequency exceeding the amplitude threshold 204 may indicate that the graduated marks 130 are sufficiently in the field of view 162 such that an accurate measurement may be taken by the processing module 250. In turn, the processing module 250 may be operative to proceed with measurement of the pitch of the gradated marks 130 as described above using the FFT processing described. In an embodiment, a subsequent instances of a given frequency exceeding the amplitude threshold 204 may be required to trigger the controller 206 to stop the syringe 100. For example, regular or semi-regular markings on the syringe 100 (e.g., corresponding to text or the like) may produce frequency information in the frequency domain plot 178. By ensuring that adjacent instances of measurement area data 176 agree in relation to a frequency that exceeds the amplitude threshold 204 may reduce the potential that the marks being measured are not the graduated marks 130 of the syringe 100.

With returned reference to FIG. 2, a volume determination module 262 may also be provided. The volume determination module 262 may receive information for a given syringe 100 regarding the pitch length of the graduated marks 130. In turn, the volume determination module 262 may be operative to compute a volume of a syringe 100 per one graduated mark 130 based on the pitch of the plurality of graduated marks 130. The volume determination module 262 may calculate the volume of the syringe 100 per one graduated mark 130 based on a diameter of the syringe 100. The diameter of the syringe 100 may be input by a user or otherwise measured by the vision system 150 or other apparatus that provides the diameter information to the volume determination module 262.

In any regard, the volume determination module 262 may store a plurality of standard volume values. For example, standard volume values for a given graduated mark 130 of a syringe 100 may comprise 0.01 mL, 0.1 mL, 0.2 mL, 0.5 mL, or some other standard volume. The volume determination module 262 may compare the calculated volume per one graduated mark 130 to the standard volumes stored in the volume determination module 262 to determine which of the standard volumes the calculated volume most closely approximates. For instance, if the calculated volume is 0.11 mL, the volume determination module 262 may consider 0.1 mL to be the closest standard volume to the calculated volume.

In turn, once the standard volume per one graduated mark 130 is known, the volume determination module 262 may also calculate the linear travel of a syringe plunger 112 for a given order to be filled into the syringe 100. In this regard, the volume determination module 262 may divide an ordered volume by the standard volume per one graduated mark. This may provide the number of graduated marks that the plunger 112 is to travel such that the plunger 112 aligns with the appropriate graduated mark 130 of the syringe for the ordered volume. In turn, this number of graduated marks 130 may be multiplied by the pitch length of the syringe to calculate the distance of linear travel the plunger 112 is to undergo to fill the syringe to the appropriate graduated mark 130 for the ordered volume.

The volume determination module 262 may further verify this amount prior to filling by comparing the distance of linear travel required to a measured length of the syringe 100. The measured length of the syringe 100 may be input by a user and/or otherwise measured in the system 150 or by another system in operative communication with the vision system 150. If the distance of linear travel of the plunger 112 required for an order exceeds the length of the syringe 100, an error may be returned and the syringe 100 may be discarded or rejected from the vision system 150. If the distance of linear travel of the plunger 112 does not exceed the length of the syringe 100, the volume determination module 262 and/or processing module 250 may output the distance of linear travel to a filling system for a syringe filler. In this regard, the syringe 100 may be filled by retracting the plunger 112 a given distance such that the plunger 112 may be aligned with the graduated mark 130 corresponding to the ordered volume.

Figure 12:
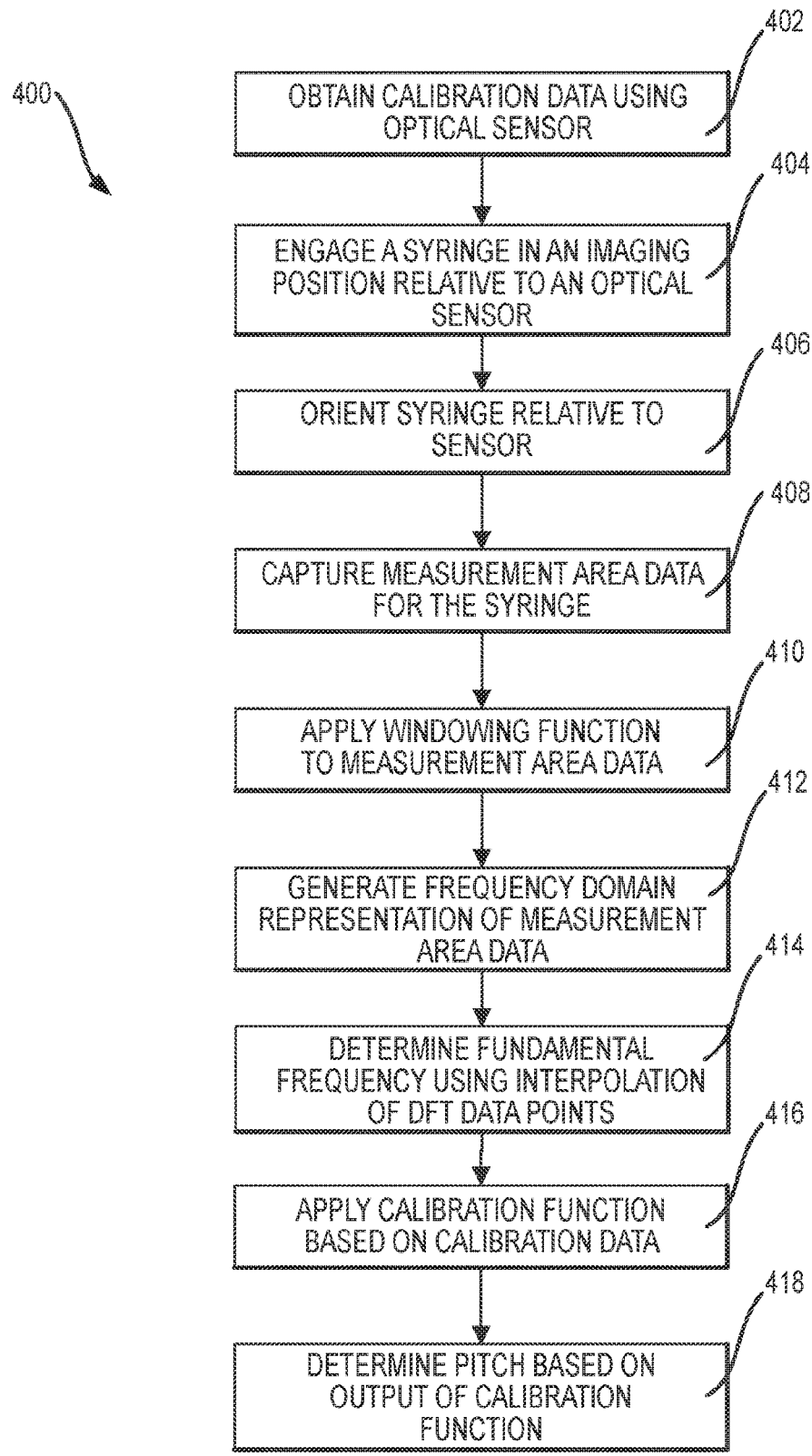
FIG. 12 depicts an embodiment of a method for determination of a pitch of graduated marks on a syringe using a vision system.
Figure 13:
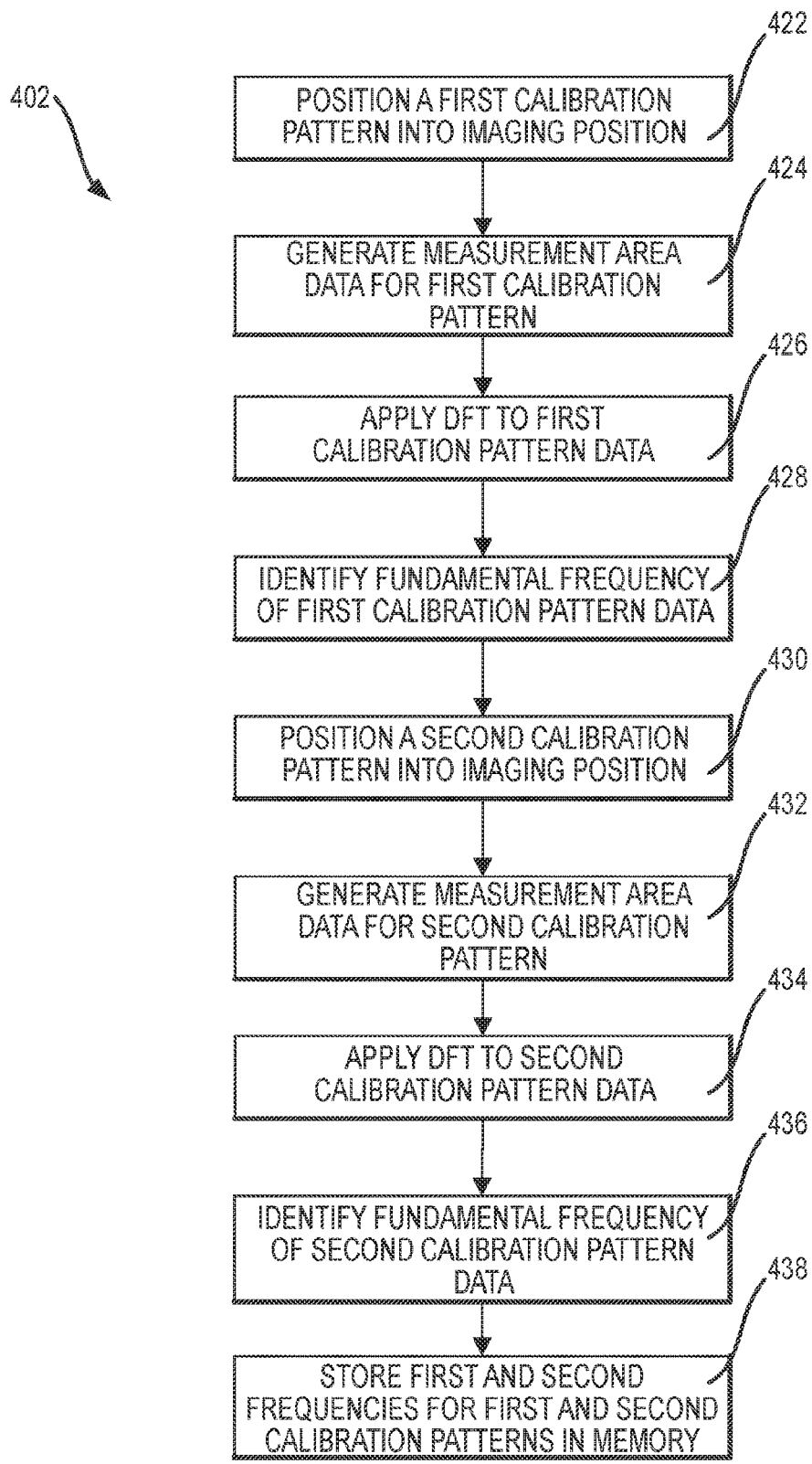
FIG. 13 depicts an embodiment of a method for calibration of a vision system for measurement of a pitch of graduated marks on a syringe to reduce or eliminate geometric distortions in the system.

With further reference to FIG. 12, an embodiment of a method 400 for measurement of a pitch of a plurality graduated marks on syringe is depicted. The method 400 may begin by obtaining 402 calibration data using an optical sensor of a vision system. With reference to FIG. 13, the obtaining 402 may include positioning 422 a first calibration pattern into the imaging position. The obtaining 402 may further include generating 424 measurement area data for the first calibration pattern and applying 426 a discrete Fourier transform to the first calibration pattern data. In turn, the obtaining 402 may include identifying 428 a fundamental frequency for the first calibration pattern data from the discrete Fourier transform. The obtaining 402 may also include positioning 430 a second calibration pattern into the imaging position. The obtaining 402 may in turn include generating 432 measurement area data for the second calibration pattern and applying 434 a discrete Fourier transform to the second calibration pattern data. In turn, the obtaining 402 may include identifying 436 a fundamental frequency of the second calibration pattern data. Finally, the obtaining 402 may include storing 438 the first and second fundamental frequencies for the first and second calibration patterns in memory for later use in the method 400.

Figure 14:
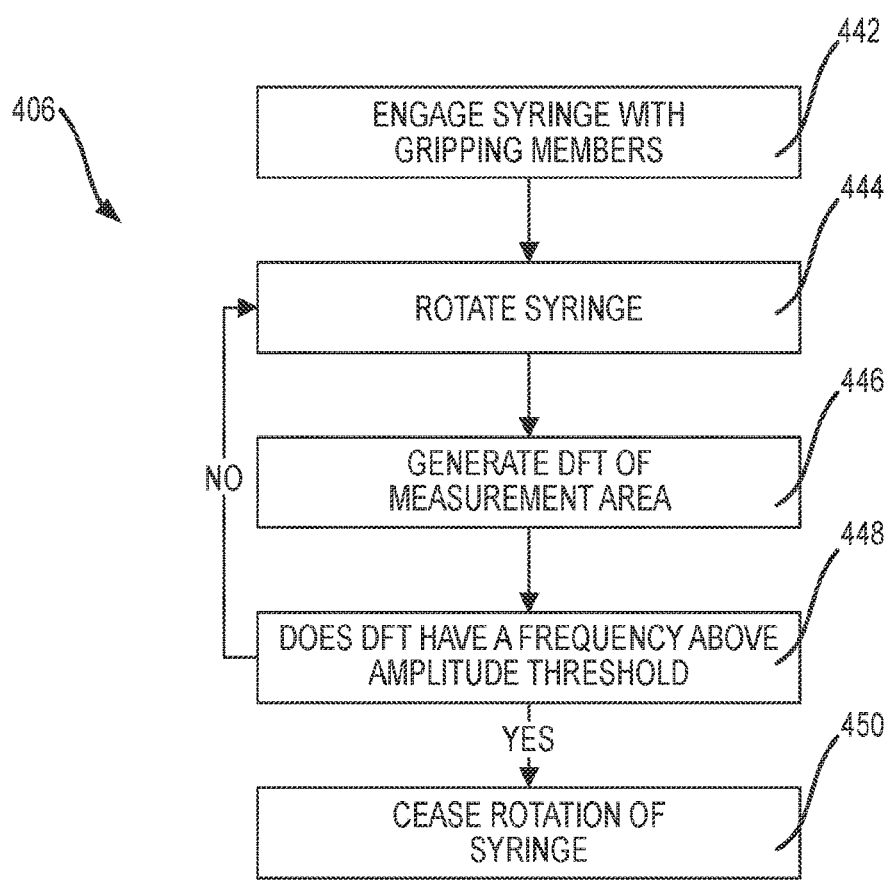
FIG. 14 depicts an embodiment of a method for orienting a syringe relative to a vision system.

Returning to FIG. 12, the method 400 may also include engaging 404 a syringe such that the syringe is disposed in the imaging position relative to the optical sensor. The method 400 may include orienting 406 the syringe relative to the optical sensor. FIG. 14 depicts details of an embodiment of the orienting 406. Specifically, the orienting 406 may include engaging 442 the syringe with gripping members. The orienting 406 may further include rotating 444 the syringe by actuation of an actuator capable of imparting rotation to the gripping members. During rotation 444, a discrete Fourier transform may be generated 446 of the measurement area data. It may be determined 448 whether the discrete Fourier transform has a frequency above a predetermined amplitude threshold. If the discrete Fourier transform does not include a frequency above the amplitude threshold, the orienting 406 may continue by rotating 444 the syringe and repeating the generating 446 and determining 448 steps. If it is determined 448 that the discrete Fourier transform includes a frequency above the amplitude threshold, the orienting 406 may proceed by ceasing 450 rotation of the syringe.

Returning to FIG. 12, after orienting 406 the syringe relative to the optical sensor, the method 400 may include capturing 408 measurement area data for the syringe. The method 400 may also include applying 410 a windowing function to the measurement area data to generate a windowed signal corresponding to the measurement area data. The windowed signal may be use to generate 412 a frequency domain representation of the measurement area data. For example, this may include applying a discrete Fourier transform to the windowed measurement area data. As a discrete Fourier transform may be used, the method 400 may include determining 414 a fundamental frequency of the discrete Fourier transform of the measurement area data using interpolation of the discrete Fourier transform data points. After determining 414 the fundamental frequency using interpolation, the method 400 may include applying 416 a calibration function 416 based on the calibration data previously obtained 402. As a result of the application 416 of the calibration function, the method 400 may include determining 418 the pitch based on output of the calibration function 418.

Figure 15:
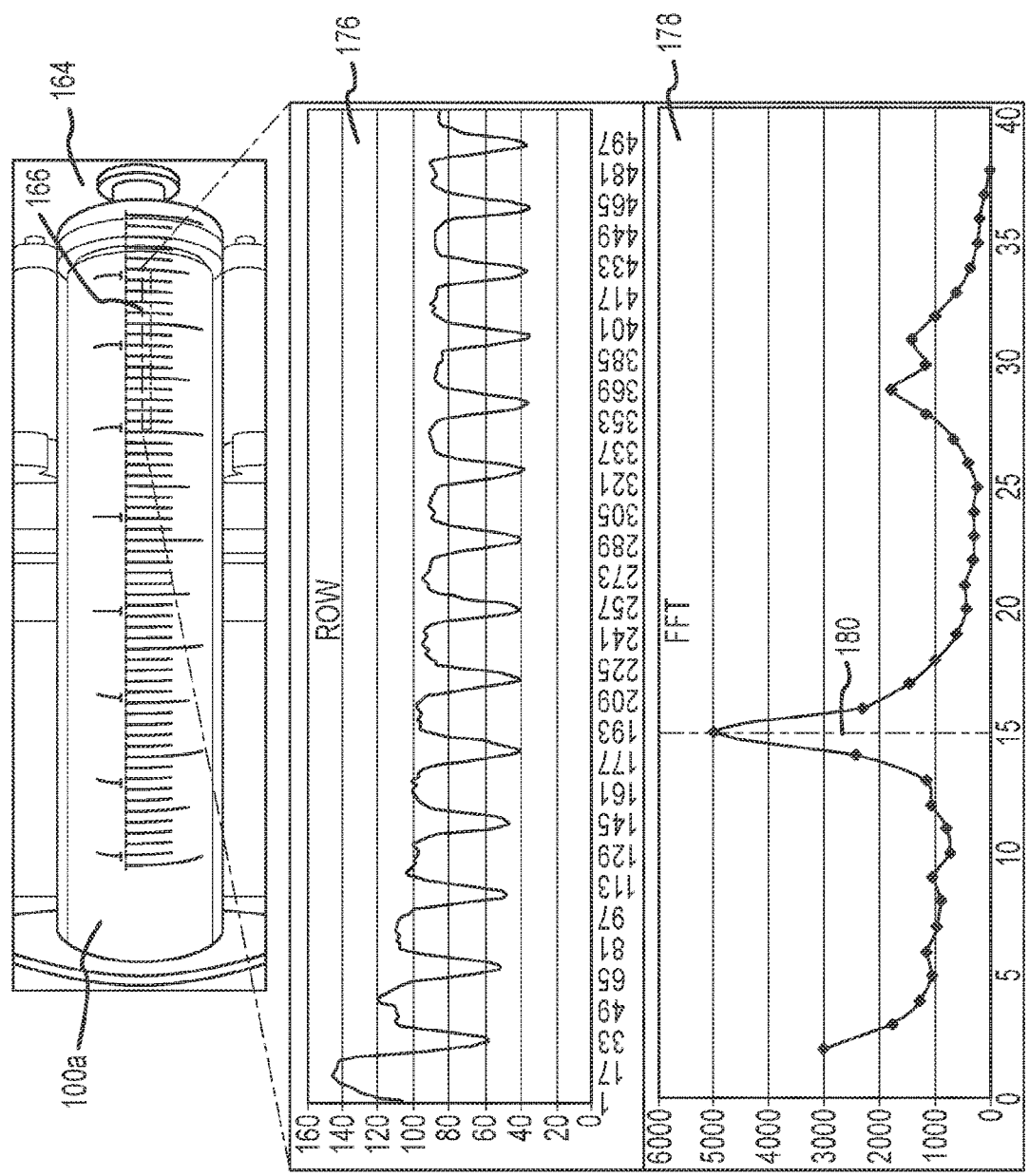
FIGS. 15 and 16 depict examples of measurement data for two different syringes measured using a vision system.
Figure 16:
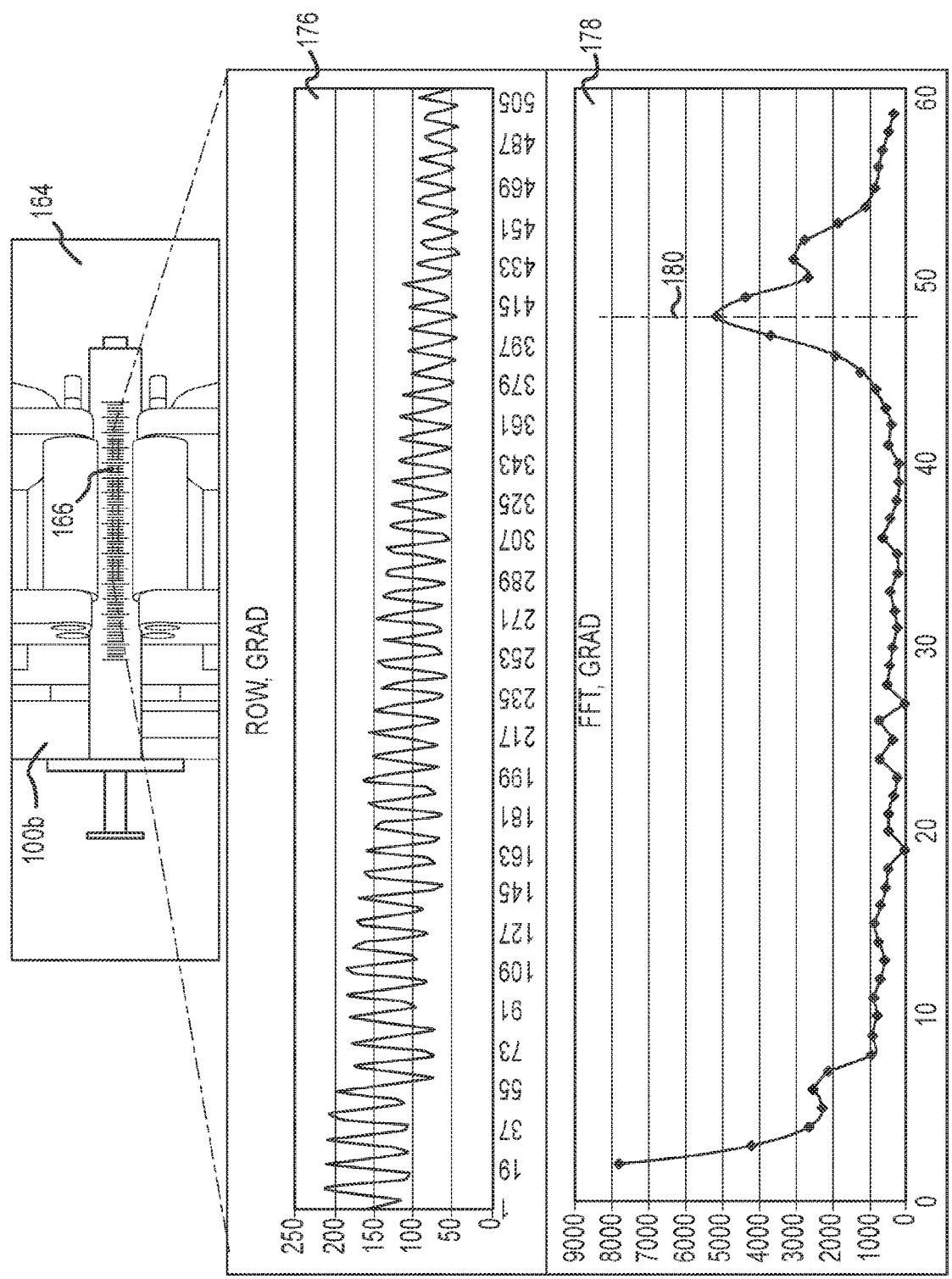

FIGS. 15 and 16 depict two examples of applications of the techniques described herein to determine pitches for two examples of different syringes 100a and 100b. In FIG. 15, a first syringe 100a is shown such that a plurality of graduated marks 130 appear within the measurement area 166. In turn, a plot 176 depicting the measurement area data 176 corresponding to the measurement area 166 (e.g., an average of plurality of rows of pixels within the measurement area 166) is shown. The measurement area data 166 maybe transformed into the frequency domain as represented in the frequency domain plot 178. Accordingly, a fundamental frequency 180 for the first syringe 100a may be determined and utilized (e.g., using the approaches outlined above including interpolation, windowing, and calibration) to arrive at a pitch of 1.79 mm for the first syringe 100a.

FIG. 16 depicts a second syringe 100b. As may be appreciated, the second syringe 100b has a smaller diameter than the first syringe 100a and a finer pitch of the graduated marks 130 for the syringe 100b relative to syringe 100a. The measurement area data 176 for the second syringe 100b may be taken from the measurement area 166. A frequency domain representation is depicted in the frequency domain plot 178 for the second syringe 100b. In turn, a fundamental frequency 180 may be determined for the second syringe 100b. As maybe appreciated, the fundamental frequency 180 for the second syringe 100b is relatively higher than that of the first syringe 100a. In turn, the pitch for the second syringe 100b may be determined (e.g., using the approaches outlined above including interpolation, windowing, and calibration) to be 0.58 mm. In this regard, the correspondence between the fundamental frequency and pitch size may be appreciated for the differently sized syringes 100a and 100b.

As depicted from the examples shown in FIGS. 15 and 16, the techniques for determining a pitch for a plurality graduated marks of syringes described herein may be utilized for a variety of different syringes having different characteristics. As such, the method may be applicable such that syringes of different types, different constructions, different manufacturers, or other variation may all be measured using the techniques described herein. That is, the vision system described herein may be operative regardless of the particulars of the syringe. As such, the vision system may be capable of measuring the pitch for any given syringe regardless of the size, type, configuration, manufacturer, or other variation associated with the syringe.

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Accordingly, it should be understood that only the preferred embodiment and variants thereof have been shown and described and that all changes and modifications that come within the spirit of the invention are desired to be protected.

What is claimed is:

1. A vision system for measurement of a pitch of a plurality of graduated marks on a syringe, comprising:
   an optical sensor having a field of view throughout which the optical sensor is operative to generate image data;
   a fixture engageable with a syringe to locate a syringe body of the syringe on a predetermined axis at an imaging position relative to the optical sensor such that a plurality of graduated marks on the syringe body are disposable within the field of view of the optical sensor, wherein the image data comprises measurement area data corresponding to at least one row of pixels extending perpendicularly to a direction in which each given one of the graduated marks extends on the syringe body; and
   a processing module, executed on a processor of the vision system, configured to process the measurement area data corresponding to the syringe to transform the measurement area data into a frequency domain representation of the measurement area data for the syringe that is indicative of a fundamental frequency of the measurement area data for the syringe, wherein the processing module is configured to determine a pitch of the plurality of graduated marks on the syringe body based on a known correspondence between the fundamental frequency of the measurement area data for the syringe and the pitch of the graduated marks on the syringe body,
   wherein the processing module is configured to transform the measurement area data into the frequency domain representation using a discrete Fourier transform (DFT), and the system further comprises an interpolation module, executed on the processor of the vision system, configured to interpolate the fundamental frequency using a plurality of frequency domain data points in the frequency domain representation.

2. The vision system of claim 1, wherein the plurality of frequency domain data points comprises a maximum amplitude frequency data point and a first adjacent data point of higher frequency than the maximum amplitude frequency data point and a second adjacent data point of lower frequency than the maximum amplitude frequency data point.

3. The vision system of claim 2, wherein the interpolation module is configured to apply a parabolic interpolation function to the plurality of frequency domain data points and solve for a maximum of the parabolic interpolation function corresponding to the fundamental frequency.

4. The vision system of claim 1, further comprising:
   a windowing module, executed on the processor of the vision system, configured to apply a window function to the measurement area data to generate windowed measurement area data used to transform the measurement area data into the frequency domain representation, wherein the window function does not notably affect the fundamental frequency of the measurement area data and reduces leakage distortions in the windowed measurement area data.

5. The vision system of claim 1, further comprising:
   a first calibration pattern having a plurality of calibration marks spaced at a first known calibration pitch, wherein the first calibration pattern is disposable in the imaging position relative to the optical sensor such that the measurement area data corresponds to at least one row of pixels extending perpendicularly to a direction in which each given one of the calibration marks extend; and
   a calibration module, executed on the processor of the vision system, configured to process the measurement area data for the first calibration pattern to transform the measurement area data into a frequency domain representation of the measurement area data for the first calibration pattern that is indicative of a first calibration frequency of the measurement area data for the first calibration pattern corresponding to the first known calibration pitch;
   wherein the processing module is configured to determine the pitch of the plurality of graduated marks on the syringe body using a function at least in part based on the fundamental frequency of the measurement area data for the syringe, the first known calibration pitch, and the first calibration frequency.

6. The vision system of claim 5, further comprising:
   a second calibration pattern having a plurality of calibration marks spaced at a second known calibration pitch, wherein the second calibration pattern is disposable in the imaging position relative to the optical sensor such that the measurement area data corresponds to at least one row of pixels extending perpendicularly to a direction in which each given one of the calibration marks extend; and
   wherein the calibration module is configured to process the measurement area data for the second calibration pattern to transform the measurement area data into a frequency domain representation of the measurement area data for the second calibration pattern that is indicative of a second calibration frequency of the measurement area data for the second calibration pattern corresponding to the second known calibration pitch;
   wherein the processing module is configured to determine the pitch of the plurality of graduated marks on the syringe body using a function at least in part based on the fundamental frequency of the measurement area data for the syringe, the first known calibration pitch, the second known calibration pitch, the first calibration frequency, and the second calibration frequency.

7. The vision system of claim 6, wherein the first calibration pitch and the second calibration pitch comprise a common calibration pitch.

8. The vision system of claim 7, wherein the first calibration pattern is a first distance from the optical sensor, the second calibration pattern is a second distance from the optical sensor, and the plurality of graduated marks on the syringe body are a third distance from the optical sensor.

9. The vision system of claim 8, wherein the processing module is configured to determine the pitch of the plurality of graduated marks on the syringe body using a function at least in part based on the fundamental frequency of the measurement area data for the syringe, the common calibration pitch, the first calibration frequency, the second calibration frequency, the first distance, and the second distance.

10. The vision system of claim 1, wherein the fixture further comprises:
a syringe gripping apparatus, comprising:
a plurality of gripping members disposed to engage, at a corresponding plurality of circumferentially offset locations, the syringe body located at an axially aligned position on the predetermined axis, wherein each of the plurality of gripping members comprises a corresponding roller for rotation about a longitudinal axis of the roller, wherein the longitudinal axes of the rollers of the plurality of gripping members are disposed parallel to each other and to the predetermined axis when the rollers are engaged with the syringe body, and
an actuator for driven rotation of at least one of the rollers of the plurality of gripping members, wherein upon the driven rotation each of the rollers co-rotate when the rollers are engaged with the syringe body to rotate the syringe body about the predetermined axis into a plurality of rotational orientations relative to the predetermined axis, and;
a control module, executed on the processor of the vision system, configured for control of the actuator;
wherein the control module is configured to control the actuator to rotate the syringe body about the predetermined axis such that the optical sensor captures a plurality of frames of measurement area data each corresponding to a different respective rotational orientation of the syringe about the predetermined axis;
wherein the processing module is configured to determine an amplitude of the fundamental frequency of the measurement area data for the plurality of frames of measurement area data and configured to determine when the amplitude of the fundamental frequency of the measurement area data for the plurality of frames of measurement area data exceeds a predetermined amplitude threshold;
wherein the processing module is in operative communication with the control module to cease rotation of the syringe body about the predetermined axis when the fundamental frequency of the measurement area data for the plurality of frames exceeds the predetermined amplitude threshold.

11. The vision system of claim 10, wherein the control module ceases rotation of the syringe body about the predetermined axis when the fundamental frequencies for respective consecutive frames of measurement area data do not differ greater than a predetermined value between two consecutive frames of the plurality of frames of measurement area data.

12. The vision system of claim 10, wherein the control module is configured to control a speed of the rotation of the syringe body about the predetermined axis based on a diameter of the syringe body.

13. The vision system of claim 1, wherein fundamental frequency is determined as an average of a plurality of rows of pixels extending perpendicularly to the direction in which each given one of the graduated marks extends on the syringe body.

14. The vision system of claim 13, wherein the measurement area data comprises an averaged row of pixels, wherein each pixel in the averaged row of pixels comprises an average of the image data in a corresponding column of pixels of the measurement area data corresponding to a plurality of pixel rows extending perpendicularly to the direction in which each given one of the graduated marks extends on the syringe body, and wherein a single frequency domain representation of the averaged row of pixels is generated to determine the fundamental frequency.

15. The vision system of claim 1, further comprising:
a volume determination module, executed on the processor of the vision system, configured to determine a calculated volume of the syringe per one graduated mark based on the pitch of the plurality of graduated marks on the syringe body and a diameter of the syringe body.

16. The vision system of claim 15, wherein the volume determination module is configured to compare the calculated volume of the syringe per one graduated mark to a plurality of standard volumes to determine a standard volume to which the calculated volume corresponds.

17. The vision system of claim 16, wherein the volume determination module is configured to determine a fill distance for linear travel of a syringe plunger of the syringe based on a requested fill volume divided by the standard volume multiplied by the pitch of the plurality of graduated marks on the syringe body.

18. The vision system of claim 17, wherein the volume determination module is configured to fill check by comparing the fill distance to a syringe length to determine if the fill distance exceeds the syringe length.

19. The vision system of claim 1, wherein the measurement area data corresponds to a measurement area offset along the predetermined axis from an image center of the field of view.

20. A method for measurement of a pitch of a plurality of graduated marks on a syringe, comprising:
engaging a syringe having a syringe body with a plurality of graduated marks, wherein the syringe is engaged along a predetermined axis at an imaging position relative to an optical sensor;
capturing image data corresponding to a measurement area of a field of view of the optical sensor to generate measurement area data corresponding to the measurement area, wherein the measurement area data corresponds to at least one row of pixels extending perpendicularly to a direction in which each given one of the graduated marks extends on the syringe body;
generating a frequency domain representation of the measurement area data by applying a Fourier transform to the measurement area data;
determining a fundamental frequency of the measurement area data; and
calculating a pitch of the plurality of graduated marks based on a known correspondence between the fundamental frequency of the measurement area data of the syringe and the pitch of the graduated marks on the syringe body,
wherein a processing module is configured to transform the measurement area data into the frequency domain representation using a discrete Fourier transform (DFT), and wherein an interpolation module, executed on a processor, is configured to interpolate the fundamental frequency using a plurality of frequency domain data points in the frequency domain representation.

* * * * *